United States Patent [19]

Karanewsky et al.

[11] Patent Number: 4,607,053

[45] Date of Patent: Aug. 19, 1986

[54] ARYLHYDROXAMATES USEFUL AS ANTIALLERGY AGENTS

[75] Inventors: Donald S. Karanewsky, East Windsor; Martin F. Haslanger, Lambertville, both of N.J.

[73] Assignee: E. R. Squibb & Sons, Inc., Princeton, N.J.

[21] Appl. No.: 719,935

[22] Filed: Apr. 4, 1985

Related U.S. Application Data

[63] Continuation-in-part of Ser. No. 611,251, May 17, 1984, abandoned.

[51] Int. Cl.$^4$ .................. C07C 83/10; C07C 101/72; A61K 31/19; A61K 31/235
[52] U.S. Cl. .................. 514/575; 260/500.5 H; 260/501.1; 260/501.11; 514/555; 560/20; 562/452
[58] Field of Search ............ 260/500.5 H, 501.1, 260/501.11, 453 RW; 514/575, 555; 560/20, 312; 562/452

[56] References Cited

U.S. PATENT DOCUMENTS

| | | | |
|---|---|---|---|
| 2,279,560 | 4/1942 | Dietrich | 260/500.5 H |
| 2,279,973 | 4/1942 | Dietrich | 260/500.5 H |
| 3,560,519 | 2/1971 | Burk et al. | 260/500.5 H |
| 3,900,514 | 8/1975 | Chappelow et al. | 260/500.5 H |
| 3,978,208 | 8/1976 | Okada | 260/500.5 H |
| 4,528,392 | 7/1985 | Musser et al. | 260/500.5 H |

FOREIGN PATENT DOCUMENTS 220744  8/1945  Switzerland .............. 260/500.5 H

OTHER PUBLICATIONS

Corey et al., "Rationally Designed, Potent Competitive Inhibitors of Leukotriene Biosynthesis", J. Am. Chem. Soc., 1984, 106, 1503–1504.

*Primary Examiner*—J. E. Evans
*Attorney, Agent, or Firm*—Lawrence S. Levinson; Burton Rodney

[57] ABSTRACT

Arylhydroxamates are provided having the structure

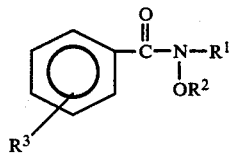

wherein
$R^1$ is hydrogen, lower alkyl, aryl, lower alkenyl, cycloalkenyl, aralkyl, or

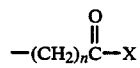

wherein n is 1 to 4 and X is hydroxy, alkoxy, amino, $C_1$–$C_4$-alkylamino or $C_1$–$C_4$-dialkylamino.
$R^2$ is hydrogen or lower alkyl; and
$R^3$ is $C_1$–$C_{20}$ alkyl or $C_3$–$C_{20}$ alkenyl, aryl, aryl-alkyl, cycloalkyl, aryl-alkenyl, lower alkoxy, lower alkenyloxy, aryl-alkoxy or cycloalkyloxy.

These compound are useful as inhibitors of $\Delta^5$-lipoxygenase and as such are useful as antiallergy agents.

33 Claims, No Drawings

ARYLHYDROXAMATES USEFUL AS ANTIALLERGY AGENTS

REFERENCE TO OTHER APPLICATIONS

This application is a continuation-in-part of pending U.S. application Ser. No. 611,251, filed May 17, 1984, now abandoned.

DESCRIPTION OF THE INVENTION

The present invention relates to arylhydroxamates which are inhibitors of $\Delta^5$-lipoxygenase and as such are useful, for example, as antiallergy agents and for treating bronchial asthma. These compounds have the structural formula

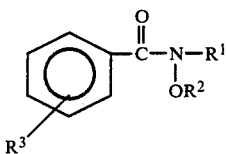         I wherein
$R^1$ is hydrogen, lower alkyl, aryl, lower alkenyl, cycloalkyl, aralkyl or

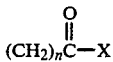

wherein n is 1 to 4 and X is hydroxy, lower alkoxy, amino, $C_1$-$C_4$-alkylamino or $C_1$-$C_4$-dialkylamino; $R^2$ is hydrogen or lower alkyl; and
$R^3$ is $C_1$-$C_{20}$ alkyl, $C_3$-$C_{20}$ alkenyl, aryl, aryl-alkyl, cycloalkyl, aryl-alkenyl, lower alkoxy, lower alkenyloxy, aryloxy, aryl-alkoxy or cycloalkyloxy, but when $R^3$ is aryl, $R^1$ is other than H. The $R^3$ group may be in the o-, m- or p-position on the benzene ring.

Where $R^1$ is

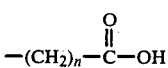

and $R^2$ is H, the above compounds may form binary or dibasic salts such as with alkali metal, such as a dilithium, disodium or dipotassium salt; where $R^1$ is other than

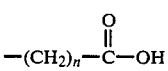

and $R^2$ is H, the above compounds will form only a monobasic salt. In addition, the compounds of formula I will form salts with dicyclohexylamine or other amines as well as with tris(hydroxymethyl)aminomethane and other amines as set out in U.S. Pat. No. 4,294,759.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent, an alkylcycloalkyl substituent, hydroxy, an alkylamino substitutent, an alkanoylamino substituent, an arylcarbonylamino substituent, a nitro substituent, a cyano substituent, a thiol substituent or an alkylthio substituent.

The term "$C_1$-$C_{20}$ alkyl" as employed herein includes the above alkyl radicals of 1 to 8 carbons and more as well as alkyl radicals of up to and including 20 carbon atoms, preferably from 4 to 16 carbons, such as in addition to the $C_4$ to $C_{12}$ alkyl radicals set out above, tridecyl, tetradecyl, pentadecyl, hexadecyl, heptadecyl, octadecyl, nonadecyl, eicosanyl including all isomers thereof with or without the above substituents.

The term "cycloalkyl" employed herein by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, an aryl group, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), 1 or 2 lower alkoxy groups, an aryl group, 1 or 2 hydroxyl groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

The term "aralkyl", "aryl-alkyl" or "aryl-lower alkyl" as used herein refers to lower alkyl groups as discussed above having an aryl substituent, such as benzyl.

The term "lower alkenyl" or "alkenyl" as employed herein by itself or as part of another group includes an unsaturated hydrocarbon group having from 3 to 8 carbons and a single carbon-carbon double bond, such as ethenyl, 1-propenyl, 2-propenyl, 1-butenyl, 2-butenyl, 3-butenyl and the like.

The term "$C_3$-$C_{20}$ alkenyl" includes straight or branched chain radicals of from 3 to 20 carbons, preferably 4 to 16 carbons in the normal chain, which include one double bond in the normal chain, such as any of the lower alkenyl grups mentioned above as well as 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 2-tridecenyl, 3-tetradecenyl, 1-pentadecenyl, 2-hexadecenyl, 4-heptadecenyl, 7-octadecenyl, 6-nonadecenyl and 8-eicosenyl, including all isomers thereof and the like.

The term "aryl-alkenyl" as used herein refers to lower alkenyl groups as discussed above having an aryl substituent.

The term "lower alkoxy", "alkoxy", "lower alkenyloxy", "cycloalkoxy" or "aralkoxy" includes any of the above lower alkyl, alkyl, lower alkenyl, cycloalkyl or aralkyl groups linked to an oxygen atom.

The term "alkanoyl" as used herein by itself or as part of another group refers to a lower alkyl group linked to a carbonyl group.

The term "halogen" or "halo" as used herein refers to chlorine, bromine, fluorine or iodine with chlorine being preferred.

Preferred are those compounds of the invention wherein $R^1$ is alkyl, such as methyl, or

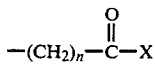

wherein n is 2 to 4, X is OH, alkoxy or amino, $R^2$ is H and $R^3$ is $C_4$ to $C_{16}$ alkyl, $C_4$-$C_{16}$ alkenyl, phenylalkyl, phenyl or phenylalkenyl and is in the para or meta position.

The various compounds of the invention may be prepared as described below.

Compounds of formula I wherein $R^2$ is H and $R^3$ is alkyl or aryl-alkyl may be prepared as follows.

The benzoic acid of the structure A

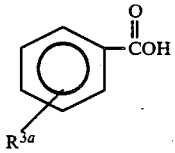

(wherein $R^{3a}$ is $C_3$-$C_{20}$ alkenyl, alkenyloxy, aryloxy, cycloalkyloxy or aryl-alkenyl) is subjected to a coupling reaction by reacting A with an O-protected hydroxyl amine of the structure B NH$_2$—O Protecting group      B (wherein the protecting group is benzyl, tetrahydropyranyl, methylthiomethyl or methoxymethyl) at a temperature of within the range of from about −15 to about 25° C., employing a molar ratio of B:A of within the range of from about 1:1 to about 2.5:1, in the presence of an activating catalyst such as 1-hydroxybenzotriazole and a coupling reagent such as N,N'-dicyclohexylcarbodiimide (DCC) and an organic base such as triethylamine to form hydroxamate II

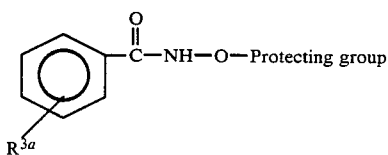

The hydroxamate II is then reacted with halide C

Hal-$R^{1a}$      C (wherein Hal is I, Br or Cl and $R^{1a}$ is the same as $R^1$ where $R^1$ is to be lower alkyl, aryl, cycloalkyl, aralkyl or

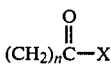

wherein X is lower alkoxy in the final product) at a temperature of within the range of from about 50 to about 110° C., employing a molar ratio of C:II of within the range of from about 1:1 to about 3:1, in the presence of a base such as sodium hydride and an inert organic solvent such as toluene or benzene to form compound III

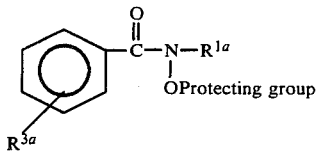

The protected compound III where the protecting group is benzyl is then subjected to hydrogenolysis (deprotection in the case of $R^1$ is benzyl) and hydrogenation by treating compound III with hydrogen in the presence of a palladium hydroxide on carbon catalyst to form the compounds of the invention IV

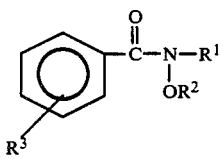

wherein $R^1$ is $(CH_2)_n$—$CO_2$alkyl, alkyl, aryl, cycloalkyl or aralkyl, $R^2$ is H and $R^3$ is $C_1$-$C_{20}$ alkyl, aryl-alkyl, cycloalkyloxy, lower alkoxy or aryloxy. However, where $R^1$ is to be

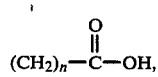

the ester group in IV may be removed by treating with an alkali metal hydroxide such as lithium hydroxide in an organic solvent such as dioxane or methanol.

Where $R^1$ in the final product is to be

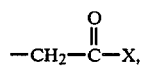

that is, n is 1, and X is OH or alkoxy, then the protected compound II will be reacted with allyl bromide (BrCH$_2$CH=CH$_2$) to form the intermediate IIIa

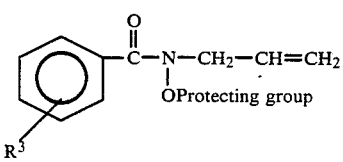

which is then treated with ozone, Jones reagent (H$_2$CrO$_4$/H$_2$SO$_4$/H$_2$O) and diazomethane to form the ester IIIb

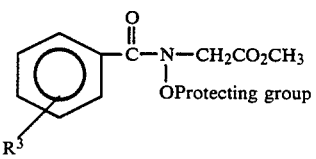

Ester IIIb may then be subjected to hydrogenolysis as described above to form the ester IVa of the invention

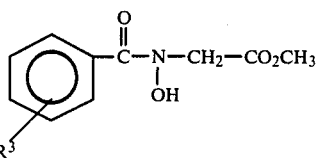

which may then be hydrolyzed to the corresponding acid IVb.

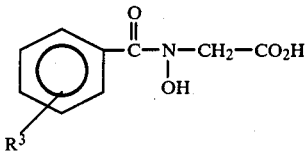

Where it is desired to form compounds wherein $R^3$ is $C_3$–$C_{20}$ alkenyl, or aryl-alkenyl and/or $R^1$ is lower alkenyl, the protecting group, where the protecting group is either tetrahydropyanyl or methoxymethyl, may be removed by treating III or IIIb with acetic acid without reducing the double bond in the $R^3$ group and/or in the $R^1$ group. Alternatively, when the protecting group is methylthiomethyl, it can be removed by treatment with $CuO$-$CuCl_2$ in aqueous acetone without reducing the double bond in the $R^3$ group or in the $R^1$ group.

Where it is desired to prepare compounds of the invention wherein $R^1$ is

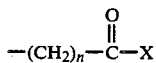

and X is amino, alkylamino or dialkylamino (wherein each alkyl of the dialkyl group is the same or different), then compound III wherein $R^1$ is

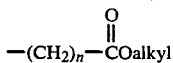

is hydrolyzed to the corresponding acid IIIA by reacting III with lithium hydroxide in the presence of a solvent such as dioxane as described above

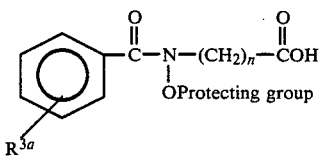

The acid IIIA is then treated with an activating agent such as isobutylchloroformate, organic base such as triethylamine and inert organic solvent such as acetonitrile and reacted with ammonium hydroxide where X is amino or with an appropriate alkylamine or dialkylamine where X is alkylamino or dialkylamino, respectively, to form amide IIIB

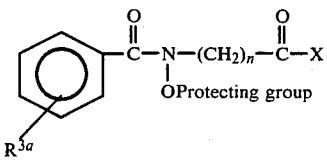

Compound IIIB where the protecting group is benzyl may then be subjected to hydrogenolysis and hydrogenation as described above to form IVA

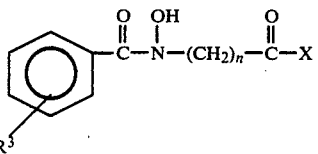

($R^3$ is alkyl and X is amino or alkylamino). Compound IIIB where the protecting group is tetrahydropyranyl may also be treated with acetic acid to remove the protecting group to form the corresponding compound wherein $R^3$ is alkenyl.

Compounds of the invention wherein $R^1$ is hydrogen may be prepared by removing the protecting group of compound II, for example, by treating II, where the protecting group is tetrahydropyranyl, with an acid catalyst such as pyridinium p-toluene sulfonate in the presence of an alcoholic solvent such as methanol, to form IIA

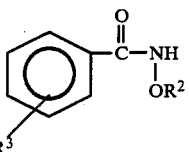

(wherein $R^2$ is hydrogen and $R^3$ is $C_3$–$C_{20}$ alkenyl) Compound IIA may be reduced as described above to form the corresponding compound wherein $R^3$ is $C_3$ to $C_{20}$ alkyl.

Preparation of compounds of formula IIA wherein $R^2$ is alkyl, that is compound V, is described hereinafter.

Compounds of the invention wherein $R^2$ is alkyl and $R^3$ is $C_1$–$C_{20}$ alkyl or aryl-alkyl may be prepared by subjecting benzoic acid A to a coupling reacting as described above except that the hydroxylamine coupling reagent employed has the structure $NH_2$—O—alkyl      D to form the hydroxamate V

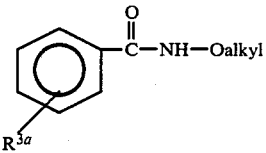

The hydroxamate V is then reacted with halide C as described above to form the compound of the invention of the structure VI

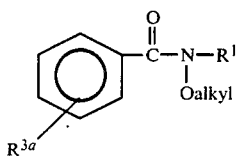

(wherein $R^{3a}$ is $C_3$-$C_{20}$ alkenyl, or aryl-alkenyl) Compound VI may be reduced as described above to form the corresponding compound wherein $R^3$ is $C_3$-$C_{20}$ alkyl and/or may be hydrolyzed (where $R^1$ is

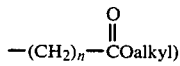

to form the corresponding acid

Compounds of formula I wherein $R^3$ is as defined above and preferably is aryl or cycloalkyl and $R^2$ is H may be prepared by treating the benzoic acid E

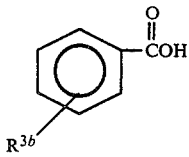

(wherein $R^{3b}$ is preferably aryl or cycloalkyl but may be any of the $R^3$ groups described above) with oxalyl chloride in the presence of an inert organic solvent such as benzene, ethyl ether or tetrahydrofuran under an inert atmosphere such as argon to form the corresponding acid chloride F

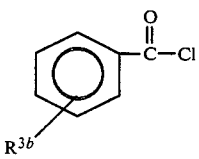

which is then reacted with a hydroxylamine G

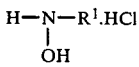

in the presence of an inert organic solvent such as tetrahydrofuran and in an organic base such as triethylamine to form the compounds of the invention VII

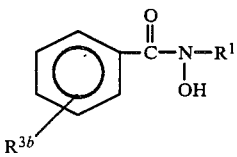

(wherein $r^{3b}$ is preferably aryl or cycloalkyl or any of the other $R^3$ groups defined above)

Compounds of formula I wherein $R^2$ is alkyl may be prepared from compound VII by treating VII with a base such as sodium hydride and an alkyl halide (Hal-Alkyl) in the presence of an inert organic solvent such as tetrahydrofuran and dimethylformamide, to form compounds of the invention VIII

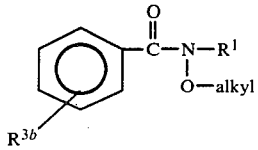

(wherein $R^{3b}$ is preferably aryl or cycloalkyl or any of the other $R^3$ groups defined above)

In an alternative method, compounds of formula I of the invention may be prepared by subjecting benzoic acid A to a coupling reaction by reacting acid A with an amine salt of the structure IX

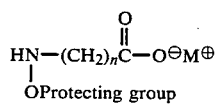

wherein the protecting group is $C_6H_5CH_2$, $CH_3SCH_2$, or tetrahydropyranyl and the like and M is an alkali metal such as Li, Na or K, or M is tetrabutylammonium, dissolved in an inert organic solvent such as dioxane, acetone, dimethylformamide or acetonitrile, in the presence of an activating agent such as isobutylchloroformate, an organic base such as triethylamine, and an inert organic solvent such as acetone, dioxane, dimethylformamide or acetonitrile. The coupling reaction is carried out at temperatures of within the range of from about $-15$ to about $25°$ C., employing a molar ratio of IX:A of within the range of from about 1:1 to about 3:1, to form the intermediate acid of the structure X

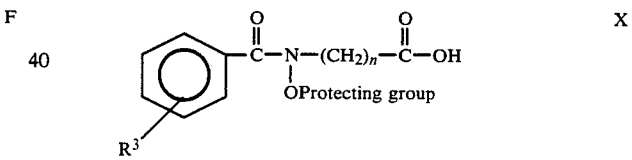

The acid X is then esterified, for example, by reacting X with a diazoalkane, such as diazomethane in ether, to form the ester XI

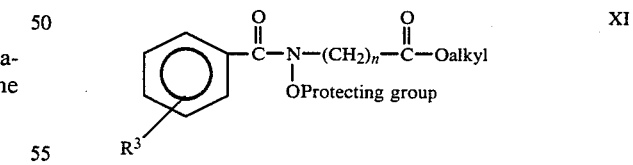

The ester XI is then subjected to a deprotecting procedure wherein XI is treated with cupric oxide and cupric chloride in an aqueous organic solvent mixture such as aqueous acetone (in the case where the protecting group is $CH_3SCH_2$—) or XI is treated with $H_2$ in the presence of a palladium hydroxide on carbon catalyst in the case where the protecting group is $C_6H_5$—$CH_2$—; the deprotected compound is then immediately hydrolyzed by treatment with lithium hydroxide or other base in the presence of an inert organic solvent such as dioxane, methanol or acetonitrile to form the acid compound of the invention of the structure XII

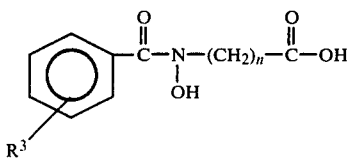 XII

The amine salt IX may be prepared from the hydroxylamine of the structure H

Protecting group —ONH$_2$  H by reacting H with acid halide J

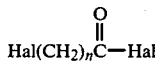 J in the presence of 2,6-lutidine and methylene choride to form the compound J Protecting group-ONHC(CH$_2$)$_n$Hal  K

Compound K is then cyclized by reacting same with a base such as sodium hydride, in the presence of benzene to form the protected N-hydroxy lactam L

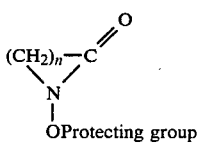 L

For the preparation of the lactam where the protecting group is CH$_3$SCH$_2$, the lactam L, where the protecting group is benzyl, can be deprotected by a hydrogenolysis reaction wherein L is treated with hydrogen in the presence of a palladium hydroxide on carbon catalyst and an inert organic solvent such as ethanol, methanol or ethyl acetate to form the hydroxy lactam XIII

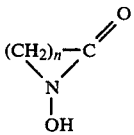 XIII

Lactam XIII can be treated with a protecting compound M

Hal—CH$_2$SCH$_3$  M
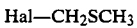

in the presence of weak base such as potassium carbonate or triethylamine and an inert organic solvent such as dimethyl formamide to form the protected compound XIV

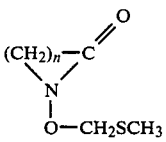 XIV

Either L or XIV is next hydrolyzed by treatment with base such as lithium hydroxide, sodium hydroxide or potassium hydroxide in the presence of dioxane to form the starting amine salt IX.

The starting benzoic acid compound A wherein R$^3$ is C$_3$–C$_{20}$alkenyl, aryl-alkyl or arylalkenyl may be prepared by reacting the formylmethylbenzoate of structure N

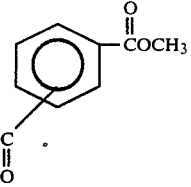 N with the phosphonium salt O

R$^4$P$^\oplus$(C$_6$H$_5$)$_3$Hal$^\ominus$  O
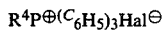

wherein R$^4$ is alkyl or aryl-alkyl containing one less carbon atom in the alkyl chain than in the alkenyl of R$^{3a}$, in the presence of n-butyllithium and hexamethylphosphorus triamide (HMPA) and an inert organic solvent such as tetrahydrofuran to form the ester A'

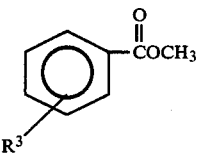 A' wherein is R$^3$ C$_3$–C$_{20}$ alkenyl or aryl-alkenyl. Hydrolysis with aqueous base gives benzoic acids A.

Compounds of formulae I and A' wherein R$^3$ is C$_1$–C$_{20}$ alkyl or aryl-alkyl may be prepared from corresponding compounds where R$^3$ is C$_3$–C$_{20}$ alkenyl or aryl-alkenyl by conventional hydrogenation techniques such as by treatment with H$_2$ in the presence of a palladium on carbon catalyst and an alcohol solvent.

The starting benzoic acids wherein R$^3$ is aryl or cycloalkyl are commercially available compounds.

The compounds of the invention are delta-5-lipoxygenase inhibitors and prevent leukotriene C$_4$ formation in macrophages (Samuelsson, B., Science, Vol. 220, p. 568-575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma, bronchial asthma and asthmoid bronchitis.

An effective but essentially non-toxic quantity of the compound is employed in treatment.

The compounds of the invention can be administered orally, parenterally or by aerosol to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution, suspension or aerosol containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in ° C. TLC plates were visualized by spraying and heating with 5% phosphomolybdic acid in ethanol. HP-20 refers to a high porous divinylbenzene-polystyrene polymer resin.

EXAMPLE 1

4-Decyl-N-hydroxy-N-methylbenzamide

A. Nonyltriphenylphosphonium Bromide (Ref. Ono Pharmaceutical Patent #J57106-651, p. 373)

A magnetically stirred suspension of 1-bromononane (Aldrich, 40 g, 0.1931M) and triphenylphosphine (101.3 g, 0.3862 mole) was heated at 100° C. (oil bath) for 2 hours. The resulting homogeneous solution was then cooled and triturated with ether (8X) to remove most of the unreacted triphenylphosphine. A viscous gum was obtained which was dissolved in $CH_2Cl_2$ and concentrated in vacuo to give the title phosphonium salt as a light yellow, extremely hygroscopic foam weighing 85 g (80.1%). TLC, neat $CH_2Cl_2$, $R_f=0.78$, PMA.

B. (Z)-Methyl 4-(1-Decenyl)benzoate (Ref. Same as for preparation of title A)

To a mixture of the title A phosphonium salt (18.22 g, 0.0332M) dissolved in anhydrous THF (200 ml) was added n-BuLi (17.6 ml of a 2.1M solution, 0.037M) at −78° C. under argon with stirring. After stirring for 30 minutes, dry hexamethylphosphorus triamide (HMPA) (29.0 ml) was added to the orange mixture. After stirring for an additional 10 minutes, p-formylmethylbenzoate (4.816 g, 0.029 mole) in dry THF (32 ml) was added dropwise over a 1.5 hours period at −78° C. Then it was warmed to 0° C. (ice bath) over a 30-minute period. $H_2O$ was added (80 ml) and the mixture extracted with ethyl acetate. The organic layer was washed with saturated $NH_4Cl$, brine, and then dried over anhydrous $MgSO_4$. Concentration in vacuo gave 18.2 g of a yellow solid which was flash chromatographed on Whatman LPS-1 silica gel eluting with (9:1) Hex: $CH_2Cl_2$. Product containing fractions were concentrated in vacuo to yield the title Wittig product as a pale yellow oil weighing 3.77 g (47%). TLC 9:1, Hex-EtOAc, $R_f=0.43$, PMA. $H^1$ NMR (60 MHz, $CDCl_3$): δ 0.87 (3H,t,—$(CH_2)_7CH_3$)

C. (Z)-4-(1-Decenyl)benzoic acid (Ref. Same as for preparation of title A)

To a stirred solution of the title B methyl ester (3.7 g, 0.0135M) in $CH_3OH$ (60 ml) and THF (10 ml) was added a 2.0N NaOH solution (21 ml) and the mixture was heated at 70° C. under argon for 2.0 hours. Concentration in vacuo left a white solid which was dissolved in EtOAc and washed with 5% $KHSO_4$ and brine, and dried over anhydrous $Na_2SO_4$. Concentration in vacuo left a white solid which was slurried in petroleum ether and filtered to give the title free acid as white crystals with m.p. = 71°-73° C. 3.03 g (84.4%) obtained. TLC (2:1) Hex-EtOAc, $R_f=0.24$, PMA. $H^1$ NMR (60 MHz, $CDCl_3$); δ0.87 (3H,t,—$(CH_2)_7CH_3$), Microanalysis Calc'd for $C_{17}H_{24}O_2$: C, 78.42, H, 9.29. Found: C, 78.29; H, 9.32.

D. (Z)-4-(1-Decenyl)-N-benzyloxybenzamide

To a stirred solution of the title C acid (3.03 g, 11.64 mM) in dry $CH_2Cl_2$ (35 ml) was added 1-hydroxybenzotriazole (1.89 g, 13.97 mM, 1.2 eq.) and N,N'-dicyclohexylcarbodiimide (2.88 g, 13.97 mM, 1.2 eq.). After one hour at room temperature under argon, O-benzylhydroxylamine hydrochloride (4.64 g, 29.1 mM, 2.5 eq.) and $Et_3N$ (4.06 ml, 29.1 mM, 2.5 eq.) were added and the mixture stirred for an additional two hours. The crude mixture was filtered (2×), evaporated, taken up in ethyl acetate, filtered again and then washed successively with 5% $KHSO_4$, saturated $NaHCO_3$, and brine. Concentration in vacuo left a white solid which was flash chromatographed on LPS-1 silica gel eluting with (9:1) Hex-EtOAc. Product containing fractions were concentrated in vacuo to a white solid which was recrystallized once from ethyl acetate-hexane to give 3.79 g (89.1%) of the desired title O-benzylhydroxamate as a white crystalline solid with m.p.=70°-71° and consistent NMR (270 MHz, $CDCl_3$) spectral data. TLC (1:1) EtOAc-Hex, $R_f$ product=0.71, UV+PMA. Microanalysis Calc'd for $C_{24}H_{31}NO_2$: C, 78.86; H, 8.55; N, 3.83. Found: C, 79.11; H, 8.66; N, 3.88.

E. (Z)4-(1-Decenyl)-N-benzyloxy-N-methylbenzamide

To a solution of the title D benzylhydroxamate (600 mg, 1.64 mM) in dry toluene (5 ml) was added prewashed NaH (45 mg, 1.80 mM) and the mixture stirred for 20 minutes at room temperature under argon. Excess methyl iodide (0.313 ml, 4.92 mM, 3 eq) was added and the mixture was refluxed for 5 hours, then cooled and partitioned between 5% $KHSO_4$ and ethyl acetate. The organic phase was washed with brine, dried over anhydrous $Na_2SO_4$ and evaporated to a yellow oil which was chromatographed on Whatman LPS-1 silica gel eluting with (3:2) pet ether-ether. Product containing fractions was evaporated to give 600 mg (96%) of the title N-methylated product as a light yellow oil with consistent NMR (60 MHz, $CDCl_3$) spectral data. TLC (1:1) Pet ether-ether, $R_f$ prod.=0.45, UV+PMA.

F. 4-Decyl-N-hydroxy-N-methylbenzamide

Argon was bubbled through a solution of the title E N-methylhydroxamate (600 mg) in $CH_3OH$ (10 ml) for 5 minutes before adding 20% palladium hydroxide on carbon (100 mg, 15% by weight) and stirring under $H_2$ for 2 hours. Mixture was then filtered through Celite, evaporated, taken up in EtOAc, filtered through a small plug of Whatman LPS-1 silica gel and evaporated to an off-white crystalline solid. One recrystallization from EtOAc-Hex gave 386 mg (84%) of the desired title N-methyl hydroxamic acid as off-white crystals with consistent NMR ($CDCl_3$, 270 MHz) spectral data. TLC (1:1) EtOAc-Hex, $R_f=0.56$, UV+PMA. m.p.=61°-63° C.

Microanalysis calcd for $C_{18}H_{29}NO_2$: C, 74.18; H, 10.03; N, 4.81. Found: C, 74.07; H, 10.02; N, 4.81.

EXAMPLE 2

(Z)-4-[[4-(1-Decenyl)benzoyl]hydroxyamino]butanoic acid

A. O-Tetrahydropyran-2-ylhydroxylamine

With gentle heating N-hydroxyphthalimide (10.0 g, 61.4 mM) was dissolved in dry $CH_2Cl_2$ (70 ml) and dioxane (80 ml), then dihydropyran (6.16 ml, 67.6 mM, 1.1 eq) and p-toluenesulfonic acid monohydrate (200 mg, 2% by weight) were added and the mixture stirred for 2 hours at room temperature under argon. The mixture was then washed successively with saturated $NaHCO_3$ (2×) and brine, dried over anhydrous $Na_2SO_4$ and evaporated to a white solid. The solid was triturated with hexane and filtered to give 13.43 g (89%) of O-tetrahydropyranyl hydroxyphthalimide as a white solid m.p. 123°-125° C. with consistent NMR (60 MHz, $CDCl_3$) spectral data. TLC (1:1) EtOAc-Hex, $R_f$=0.75, UV+PMA.

To a stirred solution of the O-THP hydroxyphthalimide (13.0 g, 52.6 mM) in dry benzene (30 ml) was added methyl hydrazine (2.82 ml, 53.0 mM) and the mixture heated at 80° C. for 15 minutes under argon. The mixture was filtered and concentrated to a 50 ml volume then vacuum distilled to give 5.46 g (89%) of the desired THP-hydroxylamine as a clear colorless oil with b.p.=70° C. (10 mm Hg). Note: Compound crystallizes upon cooling in freezer under argon. TLC (1:1) EtOAc-Hex, $R_f$0.31, UV+PMA.

B.

(Z)-4-(1-Decenyl)-N-(tetrahydropyran-2-yloxy)benzamide

To a solution of the Example 1 title C acid (1.0 g, 3.84 mM) in dry $CH_2Cl_2$ (15 ml) was added 1-hydroxybenzotriazole (623 mg, 4.61 mM, 1.2 eq) and DCC (951 mg, 4.61, 1.2 eq) and the mixture stirred for one hour under argon at room temperature. O-THP-hydroxylamine (900 mg, 7.68 mM, 2 eq) was added and the mixture stirred for 3 hours at room temperature. The mixture was filtered, evaporated, taken up in ethyl acetate, filtered again, evaporated and chromatographed on Whatman LPS-1 silica gel eluting with (8:2) Hex-EtOAc. Product containing fractions were evaporated to give 890 mg (65%) of the title coupled product as a clear, colorless oil with consistent NMR ($CDCl_3$, 270 MHz) spectral data. TLC (1:1) EtOAc-Hex, $R_f$=0.67, UV+PMA.

C.

(Z)-4-[[4-(1-Decenyl)benzoyl]tetrahydropyran-2-yloxyamino]butanoic acid, ethyl ester Prewashed NaH (70 mg, 2.9 mM, 1.2 eq) was added to a solution of the title B THP-hydroxamate (870 mg, 2.42 mM) in dry toluene (10 ml) and the mixture stirred at room temperature under argon for 15 minutes. Ethyl-4-iodobutyrate (1.76 g, 7.26 mM, 3 eq) was added and the mixture was refluxed overnight. The mixture was partitioned between 5% $KHSO_4$ and EtOAc, the organic phase washed with brine, dried over anhydrous $Na_2SO_4$ and evaporated to an oil. The crude oil was run through neutral alumina (act=1) to remove any remaining starting material eluting with (8:2) Hex-Acetone. Product fractions were evaporated and then chromatographed on Whatman LPS-1 silica gel eluting with (95:5) Hex-Acetone. Product fractions were evaporated to give 1.059 g (92%) of the desired title N-alkylated product as a clear oil with consistent NMR ($CDCl_3$, 270 MHz) spectral data. TLC (8:2) Hex-Acetone, $R_f$=0.43, UV+PMA.

D.

(Z)-4-[[4-(1-Decenyl)benzoyl]hydroxyamino]butanoic acid, ethyl ester

A stirred mixture of the title C O-THP hydroxamate (1.041 g, 2.20 mM) in (3:2:2) $HOAc:THF:H_2O$ (6 ml) was heated at 55° C. overnight under argon. The mixture was then carefully partitioned between saturated $NaHCO_3$ and EtOAc, the organic layer washed with brine, dried over anhydrous $Na_2SO_4$ and evaporated to give 897 mg (crude) of the desired title hydroxamic acid as a yellow oil. TLC (1:1) EtOAc-Hex, $R_f$0.56, UV+PMA, product streaks to baseline.

E.

(Z)-4-[[4-(1-Decenyl)benzoyl]hydroxyamino]butanoic acid

To a solution of the title D crude ethyl ester (879 mg) in dioxane (10 ml) was added a 1.0N LiOH solution (4.4 ml, 2 eq) and the mixture stirred for 1.5 hours at room temperature under argon. The mixture was then partitioned between 5% $KHSO_4$ and EtOAc, the organic phase washed with brine, dried over anhydrous $Na_2SO_4$ and evaporated to a solid. One recrystallization from EtOAc-Hex gave 638 mg (80% combined analytical yield for last 2 steps) of the desired hydroxamic acid as straw colored crystals with consistent NMR ($CDCl_3$, 270 MHz) spectral data and with m.p.=81°-83° C. TLC, EtOAc, $R_f$=0.34, UV+PMA.

Microanalysis Calcd for $C_{21}H_{31}NO_4$: C, 69.77; H, 8.64; N, 3.88. Found: C, 69.64; H, 8.70; N, 3.70.

EXAMPLE 3

(Z)-4-[[4-(1-Decenyl)benzoyl]hydroxyamino]butanoic acid

A. 4-Chloro-N-benzyloxy-butyramide

A solution of O-benzylhydroxyamine hydrochloride (22.69 g, 0.1418M) and 2,6-lutidine (33 ml, 0.2836M) in anhydrous $CH_2Cl_2$ (200 ml) was cooled to 0° C. and chlorobutyryl chloride (15.9 ml, 0.1418M) was then added dropwise under argon. The yellow mixture was stirred for 1 hour at room temperature before adding it to a 5% $KHSO_4$ solution. The organic layer was washed with saturated $NaHCO_3$, brine and then concentrated in vacuo to a white solid which was finely ground in a mortar and pestle, rinsed with hexane and filtered to yield 32 g (99%) of title chloramide as a white powder, m.p. 58°-61° C. NMR ($CDCl_3$, 60 MHz) was consistent for the desired product. TLC (1:1) EtOAc-Hex, $R_f$=0.36, PMA+UV.

B. N-Benzyloxy-piperid-2-one

To a magnetically stirred suspension of NaH (prewashed with hexanes, 1.9 g, 79.1 mM) in anhydrous benzene (100 ml) was added the title A chloramide, (15 g, 65.9 mM) dropwise in dry benzene (25 ml) at room temperature. The mixture was heated at 75° C. (oil bath). After 3 hours, another 100 mg (4.12 mM) of prewashed NaH was added and heating continued for another 3 hours. The mixture was then added carefully to cold 5% $KHSO_4$ and ethyl acetate and the organic layer washed with brine, dried over anhydrous $Na_2SO_4$ and concentrated in vacuo to a white solid (12.6 g). This was triturated with hexane, then recrystallized from ethyl acetate-hexane to give 6.05 g (48%) of title hydroxamate as white granular crystals m.p. 80°–81° C. with consistent NMR spectral data. Further product could be isolated from the mother liquor by flash chromatography.

C. N-Hydroxy-piperid-2-one

In a dry Parr bottle was added title B hydroxamate (4.0 g, 20.9 mM) dissolved in absolute ethanol (60 ml). Argon was bubbled through the solution for 5 minutes and Pd(OH)$_2$, 20% on carbon (480 mg, 12% by weight) was then added. The reaction mixture was shaken on a Parr apparatus for 3 hours, then filtered through a plug of silica gel covered with dry Celite. The filtrate was concentrated in vacuo to give 2.05 g (97%) of the desired title hydroxamic acid, as an off-white crystalline solid m.p. 82°–83° C. with consistent H$^1$-NMR spectral data. TLC (9:1) CH$_2$Cl$_2$—CH$_3$OH, R$_f$=0.30, UV and PMA single spot.

D. N-Methylthiomethoxy-piperid-2-one

To a stirred mixture of the title C hydroxamic acid (2.0 g, 19.8 mM) and chloromethyl methylsulfide (1.97 ml, 23.5 mM) in DMF (25 ml) under argon was added powdered K$_2$CO$_3$ (4.14 g, 30 mM) and the mixture stirred for 3 hours at room temperature. The yellow mixture was partitioned between 5% KHSO$_4$ and ethyl acetate, the organic layer washed with brine, dried over anhydrous Na$_2$SO$_4$, and concentrated in vacuo to a light yellow crystalline solid. The solid was slurried in petroleum ether and filtered to give 1.59 g (50%) of the desired title thioether as a white crystalline solid m.p. 64°–66° C. with consistent H$^1$-NMR (60 MHz, CDCl$_3$) spectral data. TLC (7:3, Hex-Acetone, R$_f$=0.32, PMA) single spot.

E. 4-(N-Methylthiomethoxyamino)butanoic acid, lithium salt

To a stirred mixture of the title D methyl thiomethyl ether (1.45 g, 8.99 mM) in dioxane (10 ml) was added a 1.0N lithium hydroxide solution (18 ml, 18 mM, 2 eq.) and the mixture stirred overnight under argon. The mixture was then acidified to pH 8.0 using a few drops of glacial acetic acid and the title crude lithium salt was used directly in the next coupling step. TLC (9:1, CH$_2$Cl$_2$—CH$_3$OH, R$_f$=0.35, PMA) single, more polar spot.

F. (Z)-4-[[4-(1-Decenyl)benzoyl]methylthiomethoxyamino]butanoic acid

To a stirred mixture of the Example 1 Part C acid (2.16 g, 8.3 mM) in acetone (28 ml) and Et$_3$N (1.27 ml, 9.13 mM) at −10° C. and under argon was added isobutylchloroformate (1.24 ml, 9.13 mM, 1.1 eq.) and the mixture stirred for 30 minutes at −10° C. (dry ice/acetone). The resulting mixed anhydride solution was then filtered into a dioxane solution of the title E lithium salt at −15° C., stirred for 10 minutes at −15° C., then at room temperature overnight. The reaction mixture was partitioned between 5% KHSO$_4$ and EtOAc, the organic layer washed with brine, dried over anhydrous Na$_2$SO$_4$ and concentrated in vacuo to a light yellow oil. Crude reaction mixture of the title F amide was used directly for subsequent preparation of the methyl ester. TLC (9:1, CH$_2$Cl$_2$—CH$_3$OH, R$_f$=0.19, UV and PMA).

G. (Z)-4-[[4-(1-Decenyl)benzoyl]methylthiomethoxyamino]butanoic acid, methyl ester An ethereal solution of diazomethane was added by pipette portions to a stirred, cooled (0° C., ice-H$_2$O) mixture of the crude title F acid in ether (50 ml). After 1 hour at 0° C., the mixture was rotovaped to an oil (3.55 g) which was flash chromatographed on Whatman LPS-1 silica gel eluting with EtOAc-hexane (2:8) to give title methyl ester (655 mg, 18% for overall conversion of acid to ester) as a clear oil with consistent H$^1$-NMR (CDCl$_3$, 60 MHz) spectral data. TLC (1:1, EtOAc-Hex, R$_f$=0.65, UV and PMA) single spot.

H. (Z)-4-[[4-(1-Decenyl)benzoyl]hydroxyamino]butanoic acid

Ref. Narasaka, K, et al. Bull. Chem. Soc. Japan 45, p. 3724 (1972)

(1) To a stirred solution of title G ester (523 mg, 1.24 mM) in 1% aqueous acetone (5 ml) was added CuO (198 mg, 2.47 mM, 2 eq.) and CuCl$_2$. 2H$_2$O (211 mg, 1.24 mM, 1 eq.). The mixture was stirred at room temperature for 45 minutes and then refluxed for 2.5 hours. Crude black mixture was diluted with EtOAc, filtered through Celite, washed with saturated NH$_4$Cl (3×), and filtered through anhydrous MgSO$_4$. Concentration in vacuo of the filtrate left a dark green oil which was taken up in EtOAc, washed with 1.0M H$_2$SO$_4$, dried over anhydrous Na$_2$SO$_4$ and concentrated in vacuo to a brown oil (464 mg). TLC (1:1, EtOAc-Hex, product streaks, UV and PMA) indicated 1 more polar impurity. Crude compound was used directly for subsequent hydrolysis of methyl ester.

(2) To a stirred solution of the crude methyl ester (464 mg, 1.24 mM) in dioxane (4 ml) was added a 1.0N LiOH solution (2.5 ml, 2.5 mM) and the mixture stirred at room temperature under argon for 45 minutes. The mixture was then partitioned between 5% KHSO$_4$ and EtOAc, the organic layer washed with brine, dried over anhydrous Na$_2$SO$_4$ and concentrated in vacuo to an orange oil. One recrystallization from ethyl acetate-hexane gave 305 mg of the crude title hydroxamic acid containing a more polar, baseline impurity. An HP-20 column was run to remove this impurity.

The crude acid (302 mg) was dissolved in 2 ml of 1.0N LiOH to prepare the di-lithium salt. This solution was chromatographed on an HP-20 column (200 ml bed volume, 1 inch diameter column) eluting with a gradient of H$_2$O (100%) to CH$_3$CN (100%). Product containing fractions were concentrated in vacuo to a tan oil (175 mg). The oil was dissolved in 5 ml H$_2$O, acidified with 5% KHSO$_4$, extracted with EtOAc and the organic layer washed with brine, then dried over anhydrous Na$_2$SO$_4$ and concentrated in vacuo to a light tan crystalline solid. One recrystallization from EtOAc-Hex yielded 157 mg (35%) of the title hydroxamic acid as tan crystals (m.p.=70°–72° C.) with consistent NMR (270 MHz, CDCl$_3$) spectral data. TLC (7:2:1, i-PrOH-NH$_4$OH.H$_2$, R$_f$=0.54, UV and PMA) single spot.

Microanalysis Calcd for C$_{21}$H$_{31}$NO$_4$: C, 69.78; H, 8.64; N, 3.87. Found: C, 69.60; H, 8.58; N, 3.91.

EXAMPLE 4

4-[(3-Decylbenzoyl)hydroxyamino]butanoic acid

A. 3-Formyl methylbenzoate

To a stirred solution of 3-carboxybenzaldehyde (Pfaltz & Bauer, supplier, 1.0 g, 6.66 mM) in dry THF (30 ml) at 0° C. was added by pipetted portion, an ethereal solution of diazomethane. After TLC indicated the reaction was complete, the reaction mixture was evaporated in vacuo to give 1.0 g (92%) of the desired title methyl ester as a yellow, low melting, crystalline solid with consistent NMR (CDCl$_3$, 60 MHz) spectral data. TLC (1:1) EtOAc-hex, R$_f$=0.84, UV and PMA.

B. (Z)-Methyl 3-(1-Decenyl)benzoate

To a stirred solution of the phosphonium salt CH$_3$(CH$_2$)$_8$P⊕PH$_3$Br⊖, (prepared as described in Example 1 Part A) (4.72 g, 8.6 mM, 1.4 eq.) in anhydrous THF (42 ml) under argon and maintained at −78° C. (dry ice/acetone) was added dropwise a 2.5M solution of n-butyllithium in hexanes (2.44 ml, 6.09 mM, 1 eq.). Fifteen minutes after completed addition, HMPA (6.34 ml, 36.5 mM, 6 eq.) was added to the orange-red solution followed by dropwise addition of the title A aldehyde (1.0 g, 6.09 mM) in THF (10 ml) over a 1.0 hour period. The mixture was warmed to 0° C. (ice bath) over a 30 minute period and then added to 100 ml of H$_2$O. The solution was extracted with ethyl acetate, washed with saturated NH$_4$Cl and evaporated in vacuo to an oil. The crude oil was flash chromatographed on Whatman LPS-1 silica gel eluting with (8:2) hexane-CH$_2$Cl$_2$. Product containing fractions were evaporated to give 1.436 g (86%) of the desired title Wittig product as a colorless oil with consistent NMR (CDCl$_3$, 60 MHz) spectral data. TLC (1:1) EtOAc-Hex, R$_f$=0.90, UV and PMA.

C. (Z)-3-(1-Decenyl)benzoic acid

To a stirred mixture of the title B methyl ester (1.409 g, 5.13 mM) in dioxane (20 ml) under argon was added 1.0N LiOH (7.7 ml, 7.7 mM, 1.5 eq.) and the mixture heated at 50° C. (oil bath) for 75 minutes. The mixture was cooled, partitioned between 5% KHSO$_4$ and EtOAc, the organic phase washed with brine and dried over anhydrous Na$_2$SO$_4$. Evaporation in vacuo gave 1.36 g (99%) of the desired title acid as a low melting, white crystalline solid with consistent NMR (60 MHz, CDCl$_3$) spectral data. TLC (1:1) EtOAc-hex, R$_f$ acid=0.51, UV and PMA.

D(1). 4-(N-Benzyloxyamino)butanoic acid, lithium salt

To a stirred solution of the title protected hydroxamic acid (1.5 g, 7.8 mM) from Example 3, Part B in p-dioxane (20 ml) and under argon was added 1.0N LiOH (15.7 ml, 15.7 mM). The yellow solution was then refluxed for 4 hours, cooled and then acidified to pH 8.0 with a few drops of glacial acetic acid. The crude title product mixture was then used in the next step. TLC (9:1, CH$_2$Cl$_2$—CH$_3$OH, R$_f$=0.31, PMA+UV) indicated one more polar product spot.

D(2). (Z)-4-[[3-(1-Decenyl)benzoyl]benzyloxyamino]-butanoic acid, methyl ester To a solution of the title C acid (1.35 g, 5.18 mM) in acetone (20 ml) and Et$_3$N (590 μl, 5.7 mM, 1.1 eq.) at −10° C. (dry ice/acetone) was added ethyl chloroformate (545 μl, 5.7 mM, 1.1 eq.) and the mixture stirred under argon at −10° C. for 1 hour. The mixture was filtered into a stirred, cooled (−10° C.) solution of the title D(1) lithium salt (PhCH$_2$ONH(CH$_2$)$_3$CO$_2$−Li+) in dioxane (7.11 mM, 1.4 eq.) and then stirred at room temperature under argon for 2 hours. The mixture was partitioned between 5% KHSO$_4$ and EtOAc, the organic layer washed with brine, dried over anhydrous Na$_2$SO$_4$ and evaporated in vacuo to an oil. TLC (9:1) CH$_2$Cl$_2$—CH$_3$OH, R$_f$ acid=0.41, UV and PMA.

The resulting crude acid was dissolved in ether (50 ml), cooled to 0° C. and treated with an ethereal solution of diazomethane. The crude mixture was evaporated to an oil and then chromatographed on alumina (act.=2) eluting with (9:1) hexane-acetone. Product containing fractions were concentrated in vacuo to give 1.348 g (56%) of the desired title methyl ester as a light yellow oil. TLC (1:1) EtOAc-hex, R$_f$ CH$_3$ ester=0.52, UV and PMA.

E. 4-[(3-Decylbenzoyl)hydroxyamino]butanoic acid, methyl ester

Argon was bubbled through a solution of the title D benzylhydroxamate (1.348 g, 2.9 mM) in absolute ethanol (30 ml) for 5 minutes before adding 20% palladium hydroxide on carbon (162 mg) and stirring under H$_2$ overnight. The mixture was filtered through a layered plug of Celite over Whatman LPS-1 silica gel and then evaporated to a brown oil. A flash chromatography on LPS-1 silica gel eluting with (9:1) benzene-EtOAc gave 350 mg (32%) of the desired title hydroxamic acid as a clear oil. TLC (1:1) EtOAc-hex, R$_f$=0.61, UV and PMA.

F. 4-[(3-Decylbenzoyl)hydroxyamino]butanoic acid

To a stirred solution of the title E methyl ester (350 mg, 0.927 mM) in dioxane (5 ml) was added 1.0N LiOH (1.9 ml, 1.9 mM, 2 eq.) and the mixture stirred at room temperature for 2 hours. The clear yellow solution was partitioned between 5% KHSO$_4$ and EtOAc, the organic phase washed with brine, dried over Na$_2$SO$_4$ and evaporated to an off-white crystalline solid. One recrystallization from ethyl acetate-hexane gave 191 mg (57%) of the desired title acid as straw colored crystals with m.p. 77°-79° C. and consistent NMR spectral data (270 MHz, CDCl$_3$).

Microanalysis Calcd for C$_{21}$H$_{33}$NO$_4$: C, 69.39; H, 9.15; N, 3.85. Found: C, 69.18; H, 9.14; N, 3.82.

EXAMPLE 5

4-[(2-Decylbenzoyl)hydroxyamino]butanoic acid, dilithium salt

A. 2-Formyl methylbenzoate

To a stirred solution of 2-carboxybenzaldehyde (5.0 g, 33.3 mM) in ether (100 ml) and THF (5 ml) at 0° C. was added an ethereal solution of diazomethane by pipette portions until methyl ester formation was complete (i.e., a light yellow color persists). The mixture was evaporated to give 5.48 g (98%) of the desired title aldehyde as a light yellow oil with consistent NMR (CDCl$_3$, 60 MHz) spectral data. TLC (1:1) EtOAc-Hex, R$_f$ product=0.83, UV and PMA, single spot.

B. Methyl 2-(1-Decenyl)benzoate

To a stirred, cooled (−78° C., dry ice/acetone) solution of nonyltriphenylphosphonium bromide (prepared as described in Example 1 Part A) (12.09 g, 22 mM, 1.2 eq.) in dry THF (125 ml) was added dropwise under argon a 2.5M solution of n-BuLi in hexane (7.32 ml, 18.3 mM, 1 eq.). Twenty minutes after completed addition HMPA (19 ml, 110 mM, 6 eq.) was added followed by dropwise addition of the title A aldehyde (3.0 g, 183 mM) in 25 ml of THF over a 1.5 hour period. The mixture was warmed to 0° C. (ice bath) over a 30 minute period, then added to 200 ml of $H_2O$ and extracted (2×) with ethyl acetate. The organic phase was washed with saturated $NH_4Cl$, dried over anhydrous $Na_2SO_4$ and evaporated to a thick brown oil. Crude oil was flash chromatographed on LPS-1 silica gel eluting with (8:2) Hex-$CH_2Cl_2$. Product containing fractions were evaporated to give 1.65 g (33%) of the desired title Wittig product (mixture of cis and trans isomers obtained) as a clear oil with consistent NMR ($CDCl_3$, 60 MHz) spectral data. TLC (1:1) EtOAc-Hex, $R_f$ product=0.80, UV and PMA, single spot.

C. 2-(1-Decenyl)benzoic acid

To a stirred solution of the title B methyl ester (1.61 g, 5.87 mM) in dioxane (30 ml) was added a 1.0N LiOH solution (11.7 ml, 11.7 mM, 2 eq.) and the mixture heated at 75° C. (oil bath) under argon for 2 hours. The mixture was cooled, partitioned between 5% $KHSO_4$ and EtOAc, the organic phase washed with brine, dried over anhydrous $Na_2SO_4$ and evaporated to give 1.5 g (98%) of the desired title acid as a light yellow oil with consistent NMR ($CDCl_3$, 60 MHz) spectral data. TLC (1:1) EtOAc-Hex, $R_f$ product=0.51, streaks, UV and PMS, single spot.

D. 4-(Benzyloxyamino)butanoic acid, tetrabutylammonium salt

To a stirred solution of the compound prepared in Example 3 Part B (5.74 g, 30.0 mM) in dioxane (50 ml) was added tetrabutylammonium hydroxide (36 mM, 23.4 ml of a 40% solution) under argon and the mixture stirred at room temperature overnight. Excess base was neutralized with 1.0N HCl (6 ml, 6 mM) and then the crude mixture was evaporated. Residue was azeotroped (4×) with $CH_3CN$ to insure dryness, then stored under vacuum. TLC (9:1) $CH_2Cl_2$—$CH_3OH$, $R_f$ product=0.48, UV and PMA, single spot.

E. 4-[[2-(1-Decenyl)benzoyl]benzyloxyamino]butanoic acid, methyl ester

To a cooled (0° C., ice bath) solution of the title C acid (1.65 g, 6.34 mM) in dry $CH_2Cl_2$ (10 ml) and $Et_3N$ (0.976 ml, 7.0 mM, 1.1 eq.) was added diethylchlorophosphate (1.01 ml, 7.0 mM, 1.1 eq.). The mixture was stirred for 1 hour at room temperature under argon and then 5 g of the title D salt in 5 ml of methylene chloride was added. The resulting mixture was stirred at room temperature for 2 hours. The mixture was then partitioned between 5% $KHSO_4$ and EtOAc, the organic phase washed with brine, dried over anhydrous $Na_2SO_4$ and evaporated to give a crude oil. TLC (1:1) EtOAc-Hex, $R_f$=0.23, UV and PMA.

To prepare the title methyl ester, the crude oil was dissolved in ether (45 ml) and THF (5 ml), cooled to 0° C. (ice bath) and treated with an ethereal solution of diazomethane. The reaction mixture was evaporated to an oil (3.33 g) which was taken up in $CH_2Cl_2$ and flash chromatographed on Whatman LPS-1 silica gel eluting with a (9:1) Hex-Acetone. Product containing fractions were evaporated to give 419 mg (14.2%) of the desired title hydroxamate methyl ester as a light yellow oil with consistent NMR ($CDCl_3$, 60 MHz) spectral data. TLC (9:1) EtOAc-Hex, $R_f$=0.72, both isomers are visible, UV and PMA.

F. 4-[(2-Decylbenzoyl)hydroxyamino]butanoic acid, methyl ester

Argon was bubbled through a solution of the title E benzylhydroxamate (393 mg, 0.844 mM) in absolute EtOH (15 ml) for 5 minutes before adding 20% palladium hydroxide on carbon (59 mg) and shaking the mixture under $H_2$ on a Parr apparatus for 7 hours. The mixture was filtered through a layered plug of Celite and Whatman LPS-1 silica gel and evaporated to give 300 mg (94%) of the desired title hydroxamic acid as a tan oil with consistent NMR (60 MHz, $CDCl_3$) spectral data. TLC (1:1) EtOAc-Hex, $R_f$=0.52, UV and PMA.

G. 4-[(2-Decylbenzoyl)hydroxyamino]butanoic acid, dilithium salt

To a stirred solution of the title F methyl ester (300 mg, 0.795 mM) in dioxane (4 ml) was added a 1.0N LiOH solution (1.6 ml, 1.6 mM, 2 eq.) and the mixture stirred under argon for 3 hours. The mixture was diluted with $H_2O$, extracted with ether (to remove a nonpolar impurity), the aqueous layer acidified to pH 2 with 1.0N HCl and then re-extracted with ethyl acetate. The organic phase was washed with brine, dried over anhydrous $Na_2SO_4$ and evaporated to a brown oil. TLC (9:1) $CH_2Cl_2$—$CH_3OH$, $R_f$ acid=0.11, UV and PMA.

The crude oil was dissolved in 1.0N LiOH (3 ml) and chromatographed on HP-20 eluting with a gradient of neat $H_2O$→(50:50) $H_2O$—$CH_3CN$. Product containing fractions were combined and lyophilized to give 120 mg (40%) of the desired title acid as a white powder with consistent NMR spectral data.

Microanalysis Calcd for $C_{21}H_{31}NO_4Li_2$: C, 67.19; H, 8.32; N, 3.73. Found: C, 67.58; H, 8.77; N. 3.72.

EXAMPLE 6

4-[(4-Decylbenzoyl)hydroxyamino]butanoic acid, ethyl ester

A. (Z)-4-[[4-(1-Decenyl)benzoyl]benzyloxyamino]butanoic acid, ethyl ester

Prewashed sodium hydride (188 mg, 7.52 mM, 1.1 eq.) was added to a solution of hydroxamate prepared in Example 1 Part D (2.5 g, 6.84 mM) in dry toluene (14 ml) and the mixture stirred at room temperature under argon for 15 minutes. Ethyl-4-iodobutyrate (3.31 g, 13.68 mM, 2.0 eq.) was then added and the mixture refluxed overnight. The crude mixture was cooled, partitioned between 5% $KHSO_4$ and EtOAc, the organic layer washed with brine, dried over anhydrous $Na_2SO_4$ and evaporated to an oil. The oil was dissolved in $CH_2Cl_2$ and flash chromatographed on Whatman LPS-1 silica gel eluting with (3:2) pet ether-ether. Product containing fractions were evaporated to give 2.82 g (86%) of the desired title alkylated product as a light yellow oil with consistent NMR (270 MHz, $CDCl_3$) spectral data. TLC (9:1) $CH_2Cl_2$-EtOAc, $R_f$ product=0.52, UV+PMA.

B. 4[(4-Decylbenzoyl)hydroxyamino]butanoic acid, ethyl ester

Argon was bubbled through a solution of the title B hydroxamate (481 mg, 1.003 mM) in absolute ethanol (10 ml) for 5 minutes before adding 20% palladium hydroxide on carbon (58 mg), and stirring under $H_2$ for 4 hours. The mixture was then filtered through a layered plug of Celite over LPS-1 silica gel, evaporated to a white solid and recrystallized from EtOAc-Hex to give 340 mg (87%) of the desired title hydroxamic acid as a white crystalline solid with m.p.=68°-69° C. and consistent NMR (270 MHz, $CDCl_3$) spectral data. TLC (1:1) EtOAc-Hex, $R_f$ 0.43, UV+PMA.

Microanalysis Calcd for $C_{23}H_{37}NO_4$: C, 70.55; H, 9.52; N, 3.58. Found: C, 70.64; H, 9.59; N, 3.45.

EXAMPLE 7

(Z)-4-[[4-(1-Decenyl)benzoyl]methoxyamino]butanoic acid, dicyclohexylamine salt(1:1)

A. (Z)-4-(1-Decenyl)-N-methoxybenzamide

To a solution of the benzoic acid prepared in Example 1 Part C (2.0 g, 7.68 mM) in dry $CH_2Cl_2$ (20 ml) was added 1-hydroxybenzotriazole (1.25 g, 9.22 mM, 1.2 eq.) and N,N'-dicyclohexylcarbodiimide (1.90 g, 9.22 mM, 1.2 eq.) and the mixture stirred for 1 hour at room temperature. Methoxylamine hydrochloride (1.28 g, 15.36 mM. 2 eq.) and triethylamine (2.14 ml, 15.36 mM, 2 eq.) were added, the mixture stirred for 3 hours at room temperature, then filtered, evaporated, taken up in ethyl acetate and filtered again. The organic phase was washed successively with 5% $KHSO_4$, saturated $NaHCO_3$ and brine, then dried over anhydrous $Na_2SO_4$ and evaporated to an oil. The crude oil was flash chromatographed on LPS-1 silica gel eluting with (7:3) hexane-ethyl acetate. Product containing fractions were evaporated to give 2.023 g (91%) of the desired title product, 1.664 g of cis isomer, 359 mg of trans isomer as a low melting white solid with consistent NMR ($CDCl_3$, 60 MHz) spectral data. TLC (1:1) EtOAc-Hex, $R_f$=0.39 UV and PMA.

B. (Z)-4-[[4-(1-Decenyl)benzoyl]methoxyamino]butanoic acid, ethyl ester

To a solution of the title A methyl hydroxamate (400 mg, 1.38 mM) in dry toluene (6 ml) was added prewashed NaH (38 mg, 1.52 mM) and the mixture stirred for 20 minutes at room temperature. Ethyl-4-iodobutyrate (668 mg, 2.76 mM) was added and the mixture was refluxed overnight under argon. The mixture was cooled, partitioned between 5% $KHSO_4$ and ethyl acetate and the organic phase washed with brine, dried over anhydrous $Na_2SO_4$ and evaporated to an oil. The crude oil was flash chromatographed on LPS-1 silica gel eluting with (3:2) petroleum ether-$Et_2O$. Product containing fractions were evaporated to give 539 mg (96.6%) of the desired title N-alkylated product as a light yellow oil with consistent NMR ($CDCl_3$, 270 MHz) spectral data. TLC (9:1) $CH_2Cl_2$-EtOAc, $R_f$ prod.=0.57, UV and PMA, single spot.

C. (Z)-4-[[4-(1-Decenyl)benzoyl]methoxyamino]butanoic acid

To a solution of the title B ethyl ester (435 mg, 1.08 mM) in dioxane (10 ml) was added 1.0N LiOH (2.20 ml, 2 eq.) and the mixture stirred at room temperature under argon for two hours. The mixture was then partitioned between 5% $KHSO_4$ and ethyl acetate, the organic phase washed with brine, dried over anhydrous $Na_2SO_4$ and evaporated to an oil. Crude oil was flash chromatographed on LPS-1 silica gel eluting successively with (85-15) Hex-Acetone and (95-5) $CH_2Cl_2$—$CH_3OH$. Product containing fractions were evaporated to give 234 mg (58%) of the title acid as a clear oil with consistent NMR (270 MHz, $CDCl_3$) spectral data.

D. (Z)-4-[[4-(1-Decenyl)benzoyl]methoxylamino]butanoic acid, dicyclohexylamine salt(1:1)

The dicyclohexylamine salt was prepared by dissolving the title C acid in EtOAc (1 ml) and treating it with dicyclohexylamine (126 μl, 1.1 eq.). The mixture was evaporated and then crystallized from cold petroleum ether to give 309 mg (89% conversion from acid) of the title methyl hydroxamate as the dicyclohexylamine salt.

Microanalysis Calcd for $C_{34}H_{56}N_2O_4$: C, 73.34; H, 10.14; N, 5.03. Found: C, 73.60; H, 10.26; N, 4.94.

EXAMPLE 8

N-(4-Amino-4-oxobutyl)-4-decyl-N-hydroxybenzamide

A. (Z)-4-[[4-(1-Decenyl)benzoyl]benzyloxyamino]-butanoic acid

To a solution of the ethyl ester prepared as described in Example 6 Part A (547 mg, 1.14 mM) in dioxane (5 ml) was added 1.0N LiOH (2.3 ml, 2 eq.) and the mixture stirred for 3 hours under argon at room temperature. The mixture was then partitioned between 5% $KHSO_4$ and EtOAc, the organic layer washed with brine, dried over anhydrous $Na_2SO_4$ and evaporated to give 489 mg (95%) of the title acid as a clear oil with consistent NMR (60 MHz, $CDCl_3$) spectral data. TLC (1:1) EtOAc-Hex, $R_f$ acid=0.09, UV and PMA.

B. N-(4-Amino-4-oxobutyl)-4-(1-decenyl)-N-benzyloxy benzamide

To a solution of the title A acid (489 mg, 1.08 mM) and $Et_3N$ (181 μl, 1.3 mM) in dry $CH_3CN$ (5 ml) was added isobutylchloroformate (169 μl, 1.3 mM, 1.2 eq.) and the mixture stirred for 1 hour at room temperature under argon. Concentrated $NH_4OH$ (3 ml) was added dropwise, the mixture was stirred for 30 minutes, then it was partitioned between 1.0N HCl and EtOAc. The organic layer was washed with brine, dried over anhydrous $Na_2SO_4$ and evaporated to an oil. The crude oil was chromatographed on alumina (neutral activity=2) with (1:1) EtOAc-Hex and (9:1) $CH_2Cl_2$—$CH_3OH$ followed by a chromatography on Whatman LPS-1 silica gel eluting with neat EtOAc. Product containing fractions were evaporated to give 290 mg (59%) of the title amide as a clear oil with consistent NMR ($CDCl_3$, 270 MHz) spectral data. TLC: EtOAc neat, $R_f$=0.14, UV and PMA.

C. N-(4-Amino-4-oxobutyl)-4-decyl-N-hydroxybenzamide

Argon was bubbled through a solution of the title B benzylhydroxamate (290 mg) in $CH_3OH$ (5 ml) for 5 minutes before adding 20% palladium hydroxide on carbon (35 mg, 12% by weight) and stirring under $H_2$ for 2 hours. The mixture was filtered through Celite, evaporated, taken up in EtOAc, filtered through anhydrous $MgSO_4$ powder and evaporated to an off-white solid. Two recrystallizations (from EtOAc-Hex, then acetone-Hex) gave 139 mg (60%) of the title amide as straw colored crystals with m.p.=131°–133° C. and consistent NMR (270 MHz, CDCl₃) spectral data.

Microanalysis Calcd for $C_{21}H_{34}N_2O_3$: C, 69.58; H, 9.45; N, 7.73. Found: C, 69.60; H, 9.40; N, 7.63.

EXAMPLE 9

4-[(4-Decylbenzoyl)hydroxyamino]butanoic acid

A.

(Z)-4-[[4-(1-Decenyl)benzoyl]benzyloxyamino]-butanoic acid

To a magnetically stirred solution of the benzoic acid (prepared as in Example 1 Part C) (1.97 g, 7.57 mM) in dry acetone (20 ml) at −10° C. (dry ice/acetone) and under argon was added isobutylchloroformate (1.1 ml, 8.48 mM) followed by Et₃N (1.2 ml, 7.57 mM). This was stirred for 30 minutes at −10° C., then filtered into a cooled solution (−15° C.) of the hydrolysis product prepared as described in Example 4 Part D(1). The resulting mixture was stirred for 30 minutes at −10° C. (dry ice/acetone) then allowed to warm to room temperature and stirred overnight. The reaction mixture was then partitioned between EtOAc and 5% KHSO₄. The organic layer was washed with brine, dried over anhydrous Na₂SO₄ and concentrated in vacuo to a yellow oil (5.0 g). A flash chromatography on LPS-1 silica gel eluting with (7:1) CH₂Cl₂-acetone yielded 680 mg (20%) of the title amide as a white solid with consistent NMR spectral data.

B. 4-[(4-Decylbenzoyl)hydroxyamino]-butanoic acid

The title A amide (680 mg, 1.51 mM) was dissolved in absolute ethanol (20 ml) then degassed by bubbling argon through the solution. 20% Palladium hydroxide on carbon (82 mg, 12% by weight) was added and the mixture stirred under H₂ for 2 hours. The crude mixture was then filtered through dry, packed Celite and concentrated in vacuo to a tan solid. This was dissolved in EtOAc and filtered through packed MgSO₄ (anhydrous) to remove any remaining catalyst. Concentration in vacuo left an off-white solid which was recrystallized once from EtOAc-hexane to give 410 mg (75%) of the desired product as light purple crystals with m.p.=98°–100° C. and with consistent spectral data. TLC (9:1) CH₂Cl₂—CH₃OH, $R_f$=0.23, UV+PMA.

Microanalysis Calcd for $C_{21}H_{33}NO_4$: C, 69.39; H, 9.15; N, 3.85. Found: C, 69.57; H, 9.06; N, 3.90.

EXAMPLE 10

5-[(4-Decylbenzoyl)hydroxyamino]pentanoic acid

A.

(Z)-5-[[4-(1-Decenyl)benzoyl]benzyloxyamino]pentanoic acid, ethyl ester

Prewashed NaH (51 mg, 2.11 mM, 1.1 eq.) was added to a solution of the hydroxamate prepared as described in Example 1 Part D (700 mg, 1.92 mM) in dry toluene (10 ml) and the mixture stirred for 20 minutes at room temperature under argon. Ethyl-5-iodovalerate (1.48 g, 5.76 mM, 3 eq.) was added and the mixture refluxed overnight. The mixture was then partitioned between 5% KHSO₄ and EtOAc, the organic layer washed with brine, dried over anhydrous Na₂SO₄ and evaporated to a yellow oil. The remaining starting material was removed by chromatographing on neutral alumina (act.=1) eluting with (1:1) petroleum-ether. Product fractions were evaporated, then flash chromatographed on Whatman LPS-1 silica gel eluting with (3:2) petroleum ether-ether. Product fractions were evaporated to give 760 mg (80%) of the title N-alkylated product as a clear oil with consistent NMR (CDCl₃, 270 MHz) spectral data. TLC (1:1) petroleum ether-Et₂O, $R_f$=0.42 UV and PMA.

B. 5-[(4-Decylbenzoyl)hydroxyamino]pentanoic acid, ethyl ester

Argon was bubbled through a solution of the title A benzylhydroxamate (750 mg) in methanol (10 ml) for 5 minutes, then 20% palladium hydroxide on carbon (90 mg, 12% by weight) was added and the mixture stirred under H₂ for 1 hour. The mixture was filtered through Celite, evaporated, taken up in ethyl acetate, filtered through powdered anhydrous MgSO₄ and evaporated to give 590 mg (96%) of the desired title hydroxamic acid as an off-white solid with consistent NMR (60 MHz, CDCl₃) spectral data. TLC (1:1) EtOAc-Hex, $R_f$=0.68, UV+PMA.

C. 5-[(4-Decylbenzoyl)hydroxyamino]pentanoic acid

To a solution of the title B ethyl ester (590 mg, 1.45 mM) in dioxane (8 ml) was added 1.0N LiOH (2.9 ml, 2 eq.) and the mixture stirred under argon at room temperature for 40 minutes. The mixture was then partitioned between 5% KHSO₄ and EtOAc, the organic phase washed with brine, dried over anhydrous Na₂SO₄ and evaporated to an off-white solid. One recrystallization from EtOAc-Hex gave 439 mg (80%, analytical) of the desired title acid as light purple crystals with consistent NMR(CDCl₃, 270 MHz) spectral data. TLC neat EtOAc, $R_f$=0.44, UV+PMA.

Microanalysis Calcd for $C_{22}H_{35}NO_4$: C, 69.99; H, 9.35; N, 3.71. Found: C, 69.94; H, 9.33; N, 3.80.

EXAMPLE 11

(4-Decyl-N-hydroxybenzamido)acetic acid

A. 4-Decyl benzoic acid

Argon was bubbled through a solution of the unsaturated acid prepared in Example 1 Part C (1.0 g) in CH₃OH (20 ml) for 5 minutes. 10% Palladium on carbon was added and the mix was shaken on a Parr apparatus for 4 hours under H₂. The mixture was filtered through Celite and evaporated to give 960 mg (97%) of the desired title saturated acid as a white solid with consistent NMR (CDCl₃, 60 MHz) spectral data. TLC (1:1) EtOAc-Hex, $R_f$=0.75, UV and PMA.

B. 4-Decyl-N-benzyloxybenzamide

To a solution of the title A acid (900 mg, 3.43 mM) in dry CH₂Cl₂ (15 ml) was added 1-hydroxybenzotriazole (557 mg, 4.12 mM, 1.2 eq.) and N,N′-dicyclohexylcarbodiimide (850 mg, 4.12 mM, 1.2 eq.) and the mixture stirred at room temperature under argon for 1 hour. Triethylamine (1.20 ml, 8.58 mM, 2.5 eq.) and O-benzylhydroxylamine hydrochloride (1.37 g, 8.58 mM, 2.5 eq.) were then added and the mixture stirred for 3 hours at room temperature. The mixture was filtered, evaporated, taken up in ethyl acetate and washed successively with 5% KHSO₄ and brine then dried over anhydrous Na₂SO₄ and evaporated to a white solid. Crude solid was flash chromatographed on Whatman LPS-1 silica gel eluting with (9:1) hexane-EtOAc. Product containing fractions were evaporated to give 1.11 g (87%) of the desired title benzylhydroxamate as white plates, m.p.=82°–83° C., after recrystallization from EtOAc-hexane. TLC (1:1) EtOAc-Hex, $R_f$=0.59, UV and PMA.

Microanalysis Calcd for $C_{24}H_{33}NO_2$: C, 78.44; H, 9.05; N, 3.81. Found: C, 78.32; H, 9.16; N, 3.75.

C. N-(3-Prop-1-enyl)-4-decyl-N-benzyloxy benzamide

To a solution of the title B benzylhydroxamate (500 mg, 1.36 mM) in dry toluene (6 ml) was added prewashed NaH (36 mg, 1.50 mM, 1.1 eq.) and the solution stirred at room temperature for 20 minutes before adding allyl bromide (294 µl 3.4 mM, 2.5 eq.) and refluxing overnight. The mixture was cooled, partitioned between 5% $KHSO_4$ and EtOAc, the organic layer washed with brine, dried over anhydrous $Na_2SO_4$ and evaporated to a yellow oil. Crude oil was chromatographed on neutral alumina (act.=1) eluting with (1:1) petroleum ether-ether. Product fractions were evaporated to give 510 mg (92%) of the title N-alkylated product as a light yellow oil with consistent NMR ($CDCl_3$, 270 MHz) spectral data. TLC (1:1) petroleum ether-ether, $R_f$=0.59, UV and PMA.

D. (4-Decyl-N-benzyloxybenzamido)acetic acid, methyl ester

The title C N-alkylbenzylhydroxamate (490 mg, 1.202 mM) was dissolved in EtOAc, (6 ml) cooled to −78° C. and purged with $O_2$ before bubbling ozone through the solution until a pale blue color persisted. Excess ozone was purged with bubbling $N_2$, then the ozonide solution was treated with Jones reagent (1.0 ml) at −78° C. The mixture was allowed to warm to room temperature, diluted with EtOAc and the organic phase washed successively with $H_2O$ and brine, then dried over anhydrous $Na_2SO_4$ and evaporated to a crude oil. TLC (95:5) $CH_2Cl_2$—$CH_3OH$, $R_f$=acid 0.21, UV and PMA.

The crude oil was dissolved in $Et_2O$ (10 ml), cooled to 0° C. (ice bath) and treated with an ethereal solution of diazomethane. The mixture was evaporated, and chromatographed on Whatman LPS-1 silica gel eluting with (9:1) Hex-EtOAc. Product fractions were evaporated to give 288 mg (55% for overall sequence) of the desired title methyl ester as a clear oil with consistent NMR($CDCl_3$, 270 MHz) spectral data. TLC (9:1) Hex-EtOAc, $R_f$ $CH_3$ ester=0.10, UV and PMA.

E. (4-Decyl-N-hydroxybenzamido)acetic acid, methyl ester

Argon was bubbled through a solution of the title D benzylhydroxamate (270 mg) in $CH_3OH$ (8 ml) for 5 minutes, then 20% palladium hydroxide on carbon (32 mg, 12% by weight) was added and the mixture stirred for 1 hour under $H_2$. The mixture was filtered through Celite, evaporated, taken up in EtOAc, filtered through anhydrous $MgSO_4$ and evaporated to give 213 mg (99%) of the title E hydroxamic acid as a violet, low-melting, crystalline solid. TLC (1:1) EtOAc-Hex, $R_f$=0.58 UV and PMA.

F. (4-Decyl-N-hydroxybenzamide)acetic acid

To a solution of the title E methyl ester (210 mg, 0.578 mM) was dissolved in dioxane (6 ml) was added 1.0N LiOH (1.16 ml, 1.16 mM, 2. eq.) and the mixture stirred for 20 minutes at room temperature under argon. The mixture was partitioned between 5% $KHSO_4$ and EtOAc, the organic phase washed with brine, dried over anhydrous $Na_2SO_4$ and evaporated to an off-white solid. One recrystallization from EtOAc-Hex gave 166 mg (82%) of the desired title acid as white crystals with consistent NMR (270 MHz, $CDCl_3$) spectral data. TLC (9:1) $CH_2Cl_2$—$CH_3OH$, $R_f$ 0.10, UV and PMA. m.p. 128°–130° C.

Microanalysis Calcd for $C_{19}H_{29}NO_4$: C, 68.03; H, 8.71; N, 4.18. Found: C, 67.88; H, 8.89; N, 4.19.

EXAMPLE 12

4-[[3-(1-Decenyl)benzoyl]hydroxyamino]butanoic acid

A. (Z)-3-(1-Decenyl)-N-(tetrahydropyran-2-yloxy)benzamide

To a solution of the benzoic acid prepared as described in Example 4 Part C (800 mg, 3.07 mM) in dry $CH_2Cl_2$ (12 ml) was added 1-hydroxybenzotriazole (497 mg, 3.68 mM) and DCC (759 mg, 3.68 mM) and the mixture stirred at room temperature under argon for 1 hour. O-Tetrahydropyran-2-ylhydroxylamine prepared as described in Example 2 Part A (719 mg, 6.14 mM, 2 eq.) was added, the mixture stirred for 3 hours at room temperature, then filtered and evaporated. The residue was taken up in EtOAc, filtered, evaporated and chromatographed on LPS-1 silica gel eluting successively with (7:3)→(6:4) petroleum ether-ether. Product fractions were evaporated to give 764 mg (69%) of the desired title O-THP hydroxamate as a light yellow oil with consistent NMR (270 MHz, $CDCl_3$) spectral data. TLC (1:1) $Et_2O$-petroleum ether, $R_f$=0.30, UV+-PMA.

B. (Z)-4-[[3-(1-Decenyl)benzoyl]tetrahydropyran-2-yloxyamino]butanoic acid, ethyl ester Prewashed NaH (53 mg, 2.21 mM, 1.1 eq.) was added to a solution of the title A O-THP hydroxamate (724 mg, 2.01 mM) in dry toluene (10 ml) and the mixture stirred for 30 minutes at room temperature under argon. Ethyl-4-iodobutyrate (1.46 g, 6.03 mM, 3 eq.) was added, the mixture refluxed overnight, then partitioned between 5% $KHSO_4$ and ethyl acetate. The organic phase was washed with brine, dried over anhydrous $Na_2SO_4$ and evaporated to an oil. The crude oil was purified by flash chromatography on LPS-1 silica gel eluting with a (95:5) Hex-Acetone mixture. Product fractions were evaporated to give 637 mg (67%) of the desired title N-alkylated product as a light yellow oil with consistent NMR (270 MHz, $CDCl_3$) spectral data. TLC (8:2) Hex-Acetone, $R_f$=0.47, UV+PMA.

C. 4-[[3-(1-Decenyl)benzoyl]hydroxyamino]butanoic acid, ethyl ester

A stirred solution of the title B O-THP hydroxamate (617 mg) in (3:2:2) HOAc:THF:$H_2O$ (5 ml) was heated at 55° C. overnight under argon. The mixture was then diluted with EtOAc, the organic phase washed successively with saturated $NaHCO_3$ and brine, dried over anhydrous $Na_2SO_4$ and evaporated to give 514 mg of the crude title hydroxamic acid as a light brown oil. TLC (1:1) EtOAc-Hex, $R_f$=0.52 (with streaking to baseline), UV+PMA. Compound was subsequently hydrolyzed without further purification.

D. 4-[[3-(1-Decenyl)benzoyl]hydroxyamino]butanoic acid

A solution of the title C ethyl ester (498 mg, 1.26 mM) in dioxane (6 ml) was treated with 1.0N LiOH (2.52 ml, 2 eq.) and the mixture stirred for 1.5 hours at room temperature under argon. The mixture was then partitioned between 5% KHSO₄ and EtOAc, the organic phase washed with brine, dried over anhydrous Na₂SO₄ and evaporated to an oil. The oil crystallized from hexane with cooling and scratching and was then recrystallized from EtOAc-Hex to give 380 mg (81% analytical yield for last 2 steps) of the desired title hydroxamic acid as straw colored crystals with m.p. = 71°–73° C. and with consistent NMR (270 MHz, CDCl₃) spectral data. TLC (9:1) CH₂Cl₂—CH₃OH, $R_f$ = 0.50, UV + PMA.

Microanalysis Calcd for $C_{21}H_{31}NO_4$: C, 69.77; H, 8.64, N, 3.88. Found: C, 69.56; H, 8.71; N, 3.76.

EXAMPLE 13

3-Decyl-N-hydroxy-N-methylbenzamide

Following the procedure of Example 1 except substituting m-formylmethylbenzoate for p-formylmethylbenzoate in Part B, the title compound is obtained.

EXAMPLE 14

2-Decyl-N-hydroxy-N-methylbenzamide

Following the procedure of Example 1 except substituting o-formylmethylbenzoate for p-formylmethylbenzoate in Part B, the title compound is obtained.

EXAMPLE 15

4-Decyl-N-hydroxy-N-ethylbenzamide

Following the procedure of Example 1 except substituting ethyl iodide for methyl iodide, the title compound is obtained.

EXAMPLE 16

4-Decyl-N-hydroxy-N-benzylbenzamide

Following the procedure of Example 1 except substituting benzyl bromide for methyl iodide, the title compound is obtained.

EXAMPLE 17

4-Decyl-N-hydroxy-N-propylbenzamide

Following the procedure of Example 1 except substituting propyl iodide for methyl iodide, the title compound is obtained.

EXAMPLE 18

4-Decyl-N-hydroxy-N-butylbenzamide

Following the procedure of Example 1 except substituting butyl iodide for methyl iodide, the title compound is obtained.

EXAMPLE 19

4-Decyl-N-hydroxy-N-i-butylbenzamide

Following the procedure of Example 1 except substituting i-butyl iodide for methyl iodide, the title compound is obtained.

EXAMPLE 20

4-Decyl-N-hydroxy-N-pentylbenzamide

Following the procedure of Example 1 except substituting pentyl iodide for methyl iodide, the title compound is obtained.

EXAMPLE 21

4-Decyl-N-hydroxy-N-hexylbenzamide

Following the procedure of Example 1 except substituting hexyl iodide for methyl iodide, the title compound is obtained.

EXAMPLE 22

4-Decyl-N-hydroxy-N-phenethylbenzamide

Following the procedure of Example 1 except substituting phenethyl bromide for methyl iodide, the title compound is obtained.

EXAMPLE 23

4-Decyl-N-hydroxy-N-octylbenzamide

Following the procedure of Example 1 except substituting octyl iodide for methyl iodide, the title compound is obtained.

EXAMPLE 24

4-Decyl-N-hydroxy-benzamide

Following the procedure of Example 1 except eliminating Step E, the title product is obtained.

EXAMPLE 25

4-Decyl-N-methoxy-N-methylbenzamide

Following the procedure of Example 1 except substituting methoxyamine hydrochloride for benzylhydroxyl amine hydrochloride in Part D, the title compound is obtained.

EXAMPLE 26

4-Decyl-N-ethoxy-N-ethylbenzamide

Following the procedure of Example 1 except substituting ethoxylamine hydrochloride for benzylhydroxylamine hydrochloride in Part D and substituting ethyl iodide for methyl iodide in Part E, the title compound is obtained.

EXAMPLE 27

4-Decyl-N-propoxy-N-butylbenzamide

Following the procedure of Example 1 except substituting propoxylamine hydrochloride for benzylhydroxylamine hydrochloride in Part D and substituting butyl iodide for methyl iodide in Part E, the title compound is obtained.

EXAMPLE 28

4-Decyl-N-pentoxy-N-ethylbenzamide

Following the procedure of Example 1 except substituting pentoxylamine hydrochloride for benzylhydroxylamine hydrochloride in Part D and substituting ethyl iodide for methyl iodide in Part E, the title compound is obtained.

EXAMPLE 29

4-Decyl-N-hexyloxy-N-propylbenzamide

Following the procedure of Example 1 except substituting hexyloxylamine hydrochloride for benzylhydroxylamine hydrochloride in Part D and substituting propyl iodide for methyl iodide in Part E, the title compound is obtained.

EXAMPLE 30

4-Decyl-N-ethoxy-N-benzylbenzamide

Following the procedure of Example 1 except substituting ethoxylamine hydrochloride for benzylhydroxylamine hydrochloride in Part D and substituting benzyl iodide for methyl iodide in Part E, the title compound is obtained.

EXAMPLE 31

4-Decyl-N-propoxy-N-phenethylbenzamide

Following the procedure of Example 1 except substituting propoxylamine hydrochloride for benzylhydroxylamine hydrochloride in Part D and substituting phenethyl iodide for methyl iodide in Part E, the title compound is obtained.

EXAMPLE 32

4-Decyl-N-butoxy-N-pentylbenzamide

Following the procedure of Example 1 except substituting butoxylamine hydrochloride for benzylhydroxylamine hydrochloride in Part D and substituting n-pentyl iodide for methyl iodide in Part E, the title compound is obtained.

EXAMPLE 33

4-Decyl-N-ethoxybenzamide

Following the procedure of Example 1 except substituting ethoxylamine hydrochloride for benzylhydroxylamine hydrochloride in Part D and eliminating Step E, the title compound is obtained.

EXAMPLE 34

4-Decyl-N-propoxybenzamide

Following the procedure of Example 1 except substituting propoxylamine hydrochloride for benzylhydroxylamine hydrochloride in Part D and eliminating Step E, the title compound is obtained.

EXAMPLE 35

4-(1-Decenyl)-N-methoxy-N-methylbenzamide

Following the procedure of Example 1 except substituting methoxylamine hydrochloride for benzylhydroxylamine hydrochloride in Part D, and eliminating Step F, the title compound is obtained.

EXAMPLE 36

4-(1-Decenyl)-N-ethoxy-N-ethylbenzamide

Following the procedure of Example 1 except substituting ethoxylamine hydrochloride for benzylhydroxylamine hydrochloride in Part D, substituting ethyl iodide for methyl iodide in Part E, and eliminating Step F, the title compound is obtained.

EXAMPLE 37

4-(1-Decenyl)-N-propoxy-N-butylbenzamide

Following the procedure of Example 1 except substituting propoxylamine hydrochloride for benzylhydroxylamine hydrochloride in Part D, substituting butyl iodide for methyl iodide in Part E, and eliminating Step F, the title compound is obtained.

EXAMPLE 38

4-(1-Decenyl)-N-pentoxy-N-ethylbenzamide

Following the procedure of Example 1 except substituting pentoxylamine hydrochloride for benzylhydroxylamine hydrochloride in Part D, substituting ethyl iodide for methyl iodide in Part E, and eliminating Step F, the title compound is obtained.

EXAMPLE 39

4-(1-Decenyl)-N-hexyloxyl-N-n-propylbenzamide

Following the procedure of Example 1 except substituting hexyloxylamine hydrochloride for benzylhydroxylamine hydrochloride in Part D, substituting propyl iodide for methyl iodide in Part E, and eliminating Step F, the title compound is obtained.

EXAMPLE 40

4-(1-Decenyl)-N-ethoxy-N-benzylbenzamide

Following the procedure of Example 1 except substituting ethoxylamine hydrochloride for benzylhydroxylamine hydrochloride in Part D, substituting benzy iodide for methyl iodide in Part E, and eliminating Step F, the title compound is obtained.

EXAMPLE 41

4-(1-Decenyl)-N-methoxy-N-phenethylbenzamide

Following the procedure of Example 1 except substituting methoxylamine hydrochloride for benzylhydroxylamine hydrochloride in Part D, substituting phenethyl iodide fo methyl iodide in Part E, and eliminating Step F, the title compound is obtained.

EXAMPLE 42

4-(1-Decenyl)-N-methoxy-N-ethylbenzamide

Following the procedure of Example 1 except substituting methoxylamine hydrochloride for benzylhydroxylamine hydrochloride in Part D, substituting ethyl iodide for methyl iodide in Part E, and eliminating Step F, the title compound is obtained.

EXAMPLE 43

4-(1-Decenyl)-N-ethoxybenzamide

Following the procedure of Example 1 except substituting ethoxylamine hydrochloride for benzylhydroxylamine hydrochloride in Part D, and eliminating Steps E and F, the title compound is obtained.

EXAMPLE 44

4-Undecyl-N-hydroxy-N-methylbenzamide

Following the procedure of Example 1 except substituting 1-bromodecane for 1-bromononane in Part A, the title compound is obtained.

EXAMPLE 45

4-Hexyl-N-hydroxy-N-methylbenzamide

Following the procedure of Example 1 except substituting 1-bromopentane for 1-bromononane, the title compound is obtained.

EXAMPLE 46

4-Heptyl-N-hydroxy-N-methylbenzamide

Following the procedure of Example 1 except substituting 1-bromohexane for 1-bromononane, the title compound is obtained.

EXAMPLE 47

4-Octyl-N-hydroxy-N-methylbenzamide

Following the procedure of Example 1 except substituting 1-bromoheptane for 1-bromononane, the title compound is obtained.

EXAMPLE 48

4-Nonyl-N-hydroxy-N-methylbenzamide

Following the procedure of Example 1 except substituting 1-bromooctane for 1-bromononane, the title compound is obtained.

EXAMPLE 49

4-Dodecyl-N-hydroxy-N-methylbenzamide

Following the procedure of Example 1 except substituting 1-bromoundecane for 1-bromononane, the title compound is obtained.

EXAMPLE 50

4-Pentadecyl-N-hydroxy-N-methylbenzamide

Following the procedure of Example 1 except substituting 1-bromotetradecane for 1-bromononane, the title compound is obtained.

EXAMPLE 51

3-Octyl-N-hydroxy-N-methylbenzamide

Following the procedure of Examples 1 and 13 except substituting 1-bromoheptane for 1-bromononane, the title compound is obtained.

EXAMPLE 52

3-Heptyl-N-hydroxy-N-methylbenzamide

Following the procedure of Examples 1 and 13 except substituting 1-bromohexane for 1-bromononane, the title compound is obtained.

EXAMPLE 53

3-Dodecyl-N-hydroxy-N-methylbenzamide

Following the procedure of Examples 1 and 13 except substituting 1-bromoundecane for 1-bromononane, the title compound is obtained.

EXAMPLE 54

3-Octadecyl-N-hydroxy-N-methylbenzamide

Following the procedure of Examples 1 and 13 except substituting 1-bromoheptadecane for 1-bromononane, the title compound is obtained.

EXAMPLE 55

3-Tetradecyl-N-hydroxy-N-methylbenzamide

Following the procedure of Examples 1 and 13 except substituting 1-bromotridecane for 1-bromononane, the title compound is obtained.

EXAMPLE 56

3-Hexyl-N-hydroxy-N-methylbenzamide

Following the procedure of Examples 1 and 13 except substituting 1-bromopentane for 1-bromononane, the title compound is obtained.

EXAMPLE 57

2-Hexyl-N-hydroxy-N-methylbenzamide

Following the procedure of Examples 1 and 14 except substituting 1-bromopentane for 1-bromononane, the title compound is obtained.

EXAMPLE 58

2-Octyl-N-hydroxy-N-methylbenzamide

Following the procedure of Examples 1 and 14 except substituting 1-bromoheptane for 1-bromononane, the title compound is obtained.

EXAMPLE 59

2-Undecyl-N-hydroxy-N-methylbenzamide

Following the procedure of Examples 1 and 14 except substituting 1-bromodecane for 1-bromononane, the title compound is obtained.

EXAMPLE 60

2-Pentadecyl-N-hydroxy-N-methylbenzamide

Following the procedure of Examples 1 and 14 except substituting 1-bromotetradecane for 1-bromononane, the title compound is obtained.

EXAMPLE 61

2-Heptadecyl-N-hydroxy-N-methylbenzamide

Following the procedure of Examples 1 and 14 except substituting 1-bromohexadecane for 1-bromononane, the title compound is obtained.

EXAMPLE 62

2-Nonadecyl-N-hydroxy-N-methylbenzamide

Following the procedure of Examples 1 and 14 except substituting 1-bromooctadecane for 1-bromononane, the title compound is obtained.

EXAMPLE 63

4-(1-Hexenyl)-N-hydroxy-N-methylbenzamide

Following the procedure of Example 2 except substituting 1-bromopentane for 1-bromononane in Part A and substituting methyl iodide for ethyl-4-iodobutyrate in Part C, the title compound is obtained.

EXAMPLE 64

3-(1-Heptenyl)-N-hydroxy-N-methylbenzamide

Following the procedure of Examples 2 and 13 except substituting 1-bromohexane for 1-bromononane and substituting methyl iodide for ethyl-4-iodobutyrate, the title compound is obtained.

EXAMPLE 65

3-(1-Nonenyl)-N-hydroxy-N-methylbenzamide

Following the procedure of Example 12 except substituting 1-bromooctane for 1-bromononane and methyl iodide for ethyl-4-iodobutyrate in Part B, the title compound is obtained.

EXAMPLE 66

3-(1-Undecenyl)-N-hydroxy-N-methylbenzamide

Following the procedure of Example 12 except substituting 1-bromodecane for 1-bromononane and methyl iodide for ethyl-4-iodobutyrate in Part B, the title compound is obtained.

EXAMPLE 67

3-(1-Tridecenyl)-N-hydroxy-N-methylbenzamide

Following the procedure of Example 12 except substituting 1-bromododecane for 1-bromononane and methyl iodide for ethyl-4-iodobutyrate in Part B, the title compound is obtained.

EXAMPLE 68

3-(1-Pentadecenyl)-N-hydroxy-N-methylbenzamide

Following the procedure of Example 12 except substituting 1-bromotetradecane for 1-bromononane and methyl iodide for ethyl-4-iodobutyrate in Part B, the title compound is obtained.

EXAMPLE 69

3-(1-Heptenyl)-N-hydroxy-N-methylbenzamide

Following the procedure of Example 12 except substituting 1-bromohexane for 1-bromononane and methyl iodide for ethyl-4-iodobutyrate in Part B, the title compound is obtained.

EXAMPLE 70

4-(1-Octenyl)-N-hydroxy-N-methylbenzamide

Following the procedure of Example 2 except substituting 1-bromoheptane for 1-bromononane and methyl iodide for ethyl 4-iodobutyrate in Part C, the title compound is obtained.

EXAMPLE 71

4-(1-Nonenyl)-N-hydroxy-N-methylbenzamide

Following the procedure of Example 13 except substituting 1-bromooctane for 1-bromononane and methyl iodide for ethyl 4-iodobutyrate in Part C, the title compound is obtained.

EXAMPLE 72

4-(1-Dodecenyl)-N-hydroxy-N-methylbenzamide

Following the procedure of Example 2 except substituting 1-bromoundecane for 1-bromononane and methyl iodide for ethyl 4-iodobutyrate in Part C, the title compound is obtained.

EXAMPLE 73

4-(1-Tetradecenyl)-N-hydroxy-N-methylbenzamide

Following the procedure of Example 2 except substituting 1-bromotridecane for 1-bromononane and methyl iodide for ethyl 4-iodobutyrate in Part C, the title compound is obtained.

EXAMPLE 74

4-(1-Hexadecenyl)-N-hydroxy-N-methylbenzamide

Following the procedure of Example 2 except substituting 1-bromopentadecane for 1-bromononane and methyl iodide for ethyl 4-iodobutyrate in Part C, the title compound is obtained.

EXAMPLE 75

2-(1-Eicosenyl)-N-hydroxy-N-methylbenzamide

Following the procedure of Examples 2 and 14 except substituting 1-bromononadecane for 1-bromononane and methyl iodide for ethyl 4-iodobutyrate in Part C, the title compound is obtained.

EXAMPLE 76

2-(1-Octadecyl)-N-hydroxy-N-methylbenzamide

Following the procedure of Examples 2 and 14 except substituting 1-bromoheptadecane for 1-bromononane and methyl iodide for ethyl 4-iodobutyrate in Part C, the title compound is obtained.

EXAMPLE 77

2-(1-Hexadecenyl)-N-hydroxy-N-methylbenzamide

Following the procedure of Examples 2 and 14 except substituting 1-bromopentadecane for 1-bromononane and methyl iodide for ethyl 4-iodobutyrate in Part C, the title compound is obtained.

EXAMPLE 78

2-(1-Tetradecenyl)-N-hydroxy-N-methylbenzamide

Following the procedure of Examples 2 and 14 except substituting 1-bromotridecane for 1-bromononane and methyl iodide for ethyl 4-iodobutyrate in Part C, the title compound is obtained.

EXAMPLE 79

2-(1-Dodecenyl)-N-hydroxy-N-methylbenzamide

Following the procedure of Examples 2 and 14 except substituting 1-bromoundecane for 1-bromononane and methyl iodide for ethyl 4-iodobutyrate in Part C, the title compound is obtained.

EXAMPLE 80

2-(1-Hexenyl)-N-hydroxy-N-methylbenzamide

Following the procedure of Examples 2 and 14 except substituting 1-bromopentane for 1-bromononane and methyl iodide for ethyl 4-iodobutyrate in Part C, the title compound is obtained.

EXAMPLE 81

4-[[4-Decylbenzoyl]hydroxyamino]butanoic acid

Following the procedure of Example 1 except substituting ethyl-4-iodobutyrate for methyl iodide, the title compound is obtained.

EXAMPLE 82

5-[[3-Decylbenzoyl]hydroxyamino]pentanoic acid

Following the procedure of Examples 1 and 13 except substituting ethyl-5-iodovalerate for methyl iodide, the title compound is obtained.

EXAMPLE 83

5-[[2-Decylbenzoyl]hydroxyamino]pentanoic acid

Following the procedure of Examples 1 and 14 except substituting ethyl-5-iodovalerate for methyl iodide, the title compound is obtained.

EXAMPLE 84

5-[[4-(1-Decenyl)benzoyl]hydroxyamino]pentanoic acid

Following the procedure of Example 2 except substituting ethyl-5-iodovalerate for ethyl-4-iodobutyrate, the title compound is obtained.

EXAMPLE 85

5-[[4-(1-Heptenyl)benzoyl]methoxyamino]pentanoic acid

Following the procedure of Example 7 except substituting 1-bromohexane for 1-bromononane, and ethyl-5 iodovalerate for ethyl-4-iodobutyrate and eliminating the addition of dicyclohexylamine, the title compound is obtained.

EXAMPLE 86

4-[[4-(1-Nonenyl)benzoyl]methoxyamino]butanoic acid

Following the procedure of Example 7 except substituting 1-bromooctane for 1-bromononane, and eliminating the addition of dicyclohexylamine, the title compound is obtained.

EXAMPLE 87

5-[[4-(1-Undecenyl)benzoyl]methoxyamino]pentanoic acid

Following the procedure of Example 7 except substituting 1-bromodecane for 1-bromononane, and ethyl-5 iodovalerate for ethyl-4-iodobutyrate and eliminating the addition of dicyclohexylamine, the title compound is obtained.

EXAMPLE 88

4-[[4-(1-Tridecyl)benzoyl]methoxyamino]butanoic acid

Following the procedure of Example 7 except substituting 1-bromododecane for 1-bromononane, and eliminating the addition of dicyclohexylamine, the title compound is obtained.

EXAMPLE 89

3-[[4-(1-Hexenyl)benzoyl]ethoxyamino]pentanoic acid

Following the procedure of Example 7 except substituting 1-bromopentane for 1-bromononane, ethoxylamine hydrochloride for methoxylamine hydrochloride and ethyl-3 iodovalerate for ethyl-4-iodobutyrate, and eliminating the addition of dicyclohexylamine, the title compound is obtained.

EXAMPLE 90

5-[[3-(1-Tetradecenyl)benzoyl]propoxyamino]pentanoic acid

Following the procedure of Examples 7 and 13 except substituting 1-bromotridecane for 1-bromononane, propoxylamine hydrochloride for methoxylamine hydrochloride, and ethyl-5 iodovalerate for ethyl-4-iodobutyrate and eliminating the addition of dicyclohexylamine, the title compound is obtained.

EXAMPLE 91

4-[[4-(1-Octadecenyl)benzoyl]hexyloxyamino]butanoic acid

Following the procedure of Example 7 except substituting 1-bromoheptadecane for 1-bromononane and hexyloxylamine hydrochloride for methoxylamine hydrochloride, and eliminating the addition of dicyclohexylamine, the title compound is obtained.

EXAMPLE 92

4-[[2-(1-Octenyl)benzoyl]pentyloxyamino]butanoic acid

Following the procedure of Examples 7 and 14 except substituting 1-bromoheptane for 1-bromononane, pentyloxylamine hydrochloride for methoxylamine hydrochloride, and eliminating the addition of dicyclohexylamine, the title compound is obtained.

EXAMPLE 93

(4-Dodecyl-N-hydroxybenzamido)acetic acid

Following the procedure of Example 11 except substituting 1-bromoundecane for 1-bromononane, the title compound is obtained.

EXAMPLE 94

(4-Hexyl-N-hydroxybenzamido)acetic acid

Following the procedure of Example 11 except substituting 1-bromopentane for 1-bromononane, the title compound is obtained.

EXAMPLE 95

(3-Nonyl-N-hydroxybenzamido)acetic acid

Following the procedure of Examples 11 and 13 except substituting 1-bromooctane for 1-bromononane, the title compound is obtained.

EXAMPLE 96

(4-Tetradecyl-N-hydroxybenzamido)acetic acid

Following the procedure of Example 11 except substituting 1-bromotridecane for 1-bromononane, the title compound is obtained.

EXAMPLE 97

(3-Pentadecyl-N-methoxybenzamido)acetic acid

Following the procedure of Examples 11 and 13, except substituting 1-bromotetradecane for 1-bromononane and methoxylamine hydrochloride for benzyloxylamine hydrochloride, the title compound is obtained.

EXAMPLE 98

(2-Nonadecyl-N-propoxybenzamido)acetic acid

Following the procedure of Examples 11 and 14, except substituting 1-bromooctadecane for 1-bromononane and propoxylamine hydrochloride for benzyloxylamine hydrochloride, the title compound is obtained.

EXAMPLE 99

(4-Heptyl-N-hydroxylbenzamide)acetic acid

Following the procedure of Example 11, except substituting 1-bromohexane for 1-bromononane, the title compound is obtained.

EXAMPLE 100

(3-Decyl-N-hexyloxybenzamido)acetic acid

Following the procedure of Examples 11 and 13, except substituting hexyloxylamine hydrochloride for benzyloxylamine hydrochloride, the title compound is obtained.

EXAMPLE 101

(2-Decyl-N-heptyloxybenzamido)acetic acid

Following the procedure of Examples 11 and 14, except substituting heptyloxylamine hydrochloride for benzyloxylamine hydrochloride, the title compound is obtained.

EXAMPLE 102

N-(4-Amino-4-oxobutyl)-4-octyl-N-methoxy benzamide

Following the procedure of Example 8 except substituting 1-bromoheptane for 1-bromononane and methoxylamine hydrochloride for benzyloxylamine hydrochloride, the title compound is obtained.

EXAMPLE 103

N-(4-Amino-4-oxobutyl)-4-tridecyl-N-ethoxy benzamide

Following the procedure of Example 8 except substituting 1-bromododecane for 1-bromononane and ethoxylamine hydrochloride for benzyloxylamine hydrochloride, the title compound is obtained.

EXAMPLE 104

N-(4-Amino-4-oxobutyl)-4-decyl-N-methoxy benzamide

Following the procedure of Example 8 except substituting methoxylamine hydrochloride for benzyloxylamine hydrochloride, the title compound is obtained.

EXAMPLE 105

N-(4-Amino-4-oxobutyl)-4-undecyl-N-hydroxy benzamide

Following the procedure of Example 8 except substituting 1-bromodecane for 1-bromononane, the title compound is obtained.

EXAMPLE 106

N-(5-Amino-5-oxopentyl)-2-octyl-N-ethoxy benzamide

Following the procedure of Examples 8 and 14 except substituting 1-bromoheptane for 1-bromononane, ethoxylamine hydrochloride for benzyloxylamine hydrochloride, and ethyl 3-iodovalerate for ethyl-4-iodobutyrate, the title compound is obtained.

EXAMPLE 107

N-(4-N-Ethylamino-4-oxobutyl)-3-tetradecyl-N-hydroxy benzamide

Following the procedure of Examples 8 and 13 except substituting 1-bromotridecane for 1-bromononane, and ethylamine for ammonium hydroxide, the title compound is obtained.

EXAMPLE 108

N-(4-Amino-4-oxobutyl)-4-nonadecyl-N-hydroxy benzamide

Following the procedure of Example 8 except substituting 1-bromooctadecane for 1-bromononane, the title compound is obtained.

EXAMPLE 109

(Z)-4-(1-Decenyl)-N-hydroxybenzamide

To a solution of compound prepared as described in Example 2 Part B (300 mg, 0.83 mmol) in 6 ml of $CH_3OH$ under argon was added pyridinium 4-toluenesulfonate (210 mg, 1.0 eq.). The mixture was heated to 55° C. and stirred for 4 hours. The solution was diluted with ether and washed with ½ saturated sodium chloride (20 ml) and brine (10 ml). The organic layer was dried over anhydrous $MgSO_4$ and reduced to yield a white solid. Recrystallization from hexane/EtOAc gave 200 mg (87%) of title compound as an off-white solid. TLC (1:1) Hexane:EtOAc, $R_f=0.23$, UV+PMA, product streaks to baseline.

Microanal calcd for $C_{17}H_{25}NO_2$:C, 74.14; H, 9.15; N, 5.09.

Found: C, 73.90; H, 9.27; N, 5.39.

EXAMPLE 110

(Z)-4-Decyl-N-hydroxybenzamide

Following the procedure of Example 1 Part F except substituting the Example 109 compound for the Example 1 Part E compound, the title compound is obtained.

EXAMPLE 111

3-(1-Heptenyl)-N-hydroxybenzamide

Following the procedure of Examples 109 and 13 except substituting 1-bromohexane for 1-bromononane in Example 1, Part A, the title compound is obtained.

EXAMPLE 112

4-(1-Tetradecenyl)-N-hydroxybenzamide

Following the procedure of Example 109 except substituting 1-bromotridecane for 1-bromononane in Example 1, Part A, the title compound is obtained.

EXAMPLE 113

2-(1-Dodecenyl)-N-hydroxybenzamide

Following the procedure of Examples 109 and 14 except substituting 1-bromoundecane for 1-bromononane in Example 1, Part A, the title compound is obtained.

EXAMPLE 114

4-(1-Nonadecenyl)-N-hydroxybenzamide

Following the procedure of Example 109 except substituting 1-bromooctadecane for 1-bromononane in Example 1, Part A, the title compound is obtained.

EXAMPLE 115

N-Hydroxy-N-methyl-4-(4-phenylbutyl)benzamide

A. 3-Phenylpropyl phosphonium bromide

A magnetically stirred suspension of 1-bromo-3-phenylpropane (Aldrich, 13.7 ml, 90 mmol) and triphenylphosphine (47.2 g, 180 mmole) was heated at 100° C. (oil bath) for 2 hours. The resulting white solid was then cooled and triturated with ether (5X) to remove most of the unreacted triphenylphosphine, to give the title Wittig salt in 96% yield (wt. 40 g).

B. 4-(Phenyl-1-butenyl)benzoic acid, methyl ester

To a mixture of the Part A Wittig salt under argon (6.8 g, 1.2 eq.) dissolved in anhydrous THF (70 ml) cooled to −78° C. was added n-BuLi (5.1 ml of a 2.4M solution, 1.0 eq.). After stirring for 45 minutes, distilled hexamethyl phosphorus (HMPA) (14.4 ml) was added to the orange mixture, turning it black. After stirring for an additional 15 minutes, p-formylmethylbenzoate (2.0 g, 12.2 mmole) in dry THF (10 ml) was added dropwise. After stirring for a two hour period at −78° C., it was warmed to 0° C. (ice bath) for 1 hour. H₂O was added and the mixture extracted with ethyl acetate. The organic layer was washed with saturated NH₄Cl (3×), brine, and then dried over anhydrous MgSO₄. Concentration in vacuo gave a yellow oil which was flash chromatographed on LPS-1 silica gel, eluting with (95:5) Hex:EtOAc. Product containing fractions were concentrated in vacuo to yield the title Wittig product as a light yellow oil (2.72 g, 84%). TLC (95:5) Hex-EtOAc, $R_f$=0.22 UV +PMA.

C. 4-(4-Phenyl-1-butenyl)benzoic acid

To a stirred solution of the Part B methyl ester (2.72 g, 10.2 mmol) in CH₃OH (60 ml) and THF (10 ml) was added a 2.0N NaOH solution (15.3 ml) and the mixture was refluxed under argon for 0.75 hour and quenched with 1 HCl (40.8 ml, 4.5 eq.). Concentration in vacuo to ⅓ volume left a white solid which was collected by filtration and recrystallized from hexane to yield title acid as a white solid, 2.2 g (86%). TLC (1:1) Hex-EtOAc, $R_f$=0.39, UV+PMA.

D. 4-(4-Phenyl-1-butenyl)-N-(tetrahydropyran-2-yloxy)benzamide

To a 0° C. solution of Part C acid (2.0 g, 7.9 mmol) in 40 ml of CH₂Cl₂ under argon was added N,N′-dicyclohexylcarbodiimide (DCC) (1.96 g, 1.2 eq.), 1-hydroxybenzotriazole (HOBt) (1.28 g, 1.2 eq.), tetrahydropyranyl hydroxylamine (H₂N-OTHP) (1.86 g, 2.0 eq.), sequentially. The solution was allowed to warm to room temperature after 0.5 hour and then stirred under argon for 3 hours. The solution was filtered, concentrated in vacuo, diluted with EtOAc, and refiltered. Concentration in vacuo gave a golden oil which was chromatographed on LPS-1 silica gel eluting with 7:3 hexane/EtOAc. Product containing fractions were concentrated in vacuo to yield title compound as a light yellow oil, wt. 2.8 g (~100).

E. 4-(4-Phenyl-1-butenyl)-N-methyl-N-(tetrahydropyran-2-yloxy)benzamide

To a stirring solution of Part D compound (1.8 g, 5.1 mmol) under argon in 30 ml of dry toluene was added NaH (1.1 eq., 134 mg). The mixture was allowed to stir for 30 minutes and then CH₃I (0.95 ml, 3.0 eq.) was added. The mixture was heated to reflux and allowed to stir for 1 hour. The reaction was cooled and diluted with EtOAc and partitioned over 5% KHSO₄. The organic phase was washed with brine, dried over anhydrous Na₂SO₄ and evaporated to yield yellow oil which was chromatographed on LPS-1 silica gel eluting with (6:4) hexane:EtOAc. Product containing fractions were evaporated to give title compound (1.6 g, 87%) as a clear oil. TLC (1:1) hexane:EtOAc. $R_f$=0.40, UV+PMA.

F. 4-(4-Phenylbutyl)-N-methyl-N-(tetrahydropyran-2-yloxy)benzamide

To a stirring solution of Part E compound (500 mg, 1.37 mmol) in 10 ml of CH₃OH was added rhodium/alumina (5%) (50 mg) under argon. Hydrogen gas was added and the reaction was allowed to stir under H₂ (balloon) for 0.5 hour. The mixture was filtered (Millipore) and concentrated in vacuo to yield a clear oil which was carried directly on to the next step.

G. N-Hydroxy-N-methyl-4-(4-phenylbutyl)-benzamide

To a stirring solution of Part F compound (500 mg, 1.37 mmol) in 10 ml of CH₃OH under argon was added pyridinum-p-toluenesulfonate (344 mg, 1.0 eq.). The solution was heated to 60° C. in an oil bath for 5 hours, then diluted with EtOAc and washed with 10 ml of brine, and diluted with 10 ml of water. The organic layer was washed with brine (10 ml) and dried over Na₂SO₄ (anhydrous) and reduced in vacuo to yield an oil which was crystallized from hexane/EtOAc to give title product (325 mg) (84%) as a white solid with m.p. 62°–63.5° C. TLC (1:1) hexane-EtOAc; $R_f$=0.28, UV+PMA. Product streaks to baseline.

Anal Calcd for C₁₈H₂₁NO₂: C, 76.29; H, 7.47; N, 4.94. Found: C, 76.20; H, 7.52; N, 4.68.

EXAMPLE 116

N-Hydroxy-N-methyl-4-(4-phenyl-1-butenyl)benzamide

To a solution of 4-(4-phenyl-1-butenyl)-N-methyl-N-(tetrahydropyran-2-yloxy)benzamide (prepared in Example 1 Part E) (500 mg, 1.37 mmol) in 12 ml of CH₃OH under argon was added pyridinium 4-toluenesulfonate (344 mg, 1.0 eq.). The mixture was heated to 55° C. and stirred for 2.5 hours. The solution was diluted with ether and washed with ½ saturate sodium chloride (20 ml) and brine (10 ml). The organic layer was dried over anhydrous MgSO₄ and reduced to yield a light yellow oil which was flash chromatographed on Merck silica gel, eluting with (7:3) Hex:EtOAc. Product containing fractions were concentrated in vacuo to yield title product, 426 mg (85%) as a golden oil.

TLC (1:1) Hexane:EtOAc, $R_f$=0.18, UV+PMA, product streaks to baseline. Trace Rf=0.61.

Anal Calcd for C₁₈H₁₉NO₂: C, 76.84; H, 6.81; N, 4.98. Found: C, 76.80; H, 6.76; N, 4.71.

EXAMPLE 117

N-Hydroxy-N-Methyl[1,1′-biphenylyl]-4-carboxamide

A. 1,1′-Biphenylcarboxylic acid chloride

To a stirring solution of 1,1′-biphenylcarboxylic acid (1.0 g, 4.6 mmol) in 10 ml of dry benzene, under argon was added oxalyl chloride (0.40 ml, 2.0 eq.). To this solution was added DMF dropwise in 10 minute intervals, until no gas was evolved and the solution turned slightly cloudy (two drops). The mixture was stirred for 1 hour, then reduced on the rotovap without heating. The crude product, white solid, was carried directly on to the next step.

B. N-Hydroxy-N-methyl[1,1′-biphenylyl]-4-carboxamide

To a 0° C. solution of N-methylhydroxylamine hydrochloride (771 mg, 2 eq.) in 7 ml of THF:H₂O (1:1) with triethylamine (1.43 ml, 3.0 eq.) was added Part A compound (~1.0 g, 4.6 mmol) in THF (5 ml). The solution was stirred for 2 hours at 0° C. then allowed to warm to room temperature and stir overnight. The reaction mixture was diluted with ether and the organic layer was washed with H₂O, 1N HCl (2×), and brine, then dried over anhydrous MgSO₄. Concentration in vacuo gave a crystalline white solid which was isolated by filtration and washed with hexane, dried under vacuum over P₂O₅ to yield title product, 690 mg (66% from Part A compound), as a white solid with a m.p. of 133°-134.5° C.

TLC (1:1) Hexane:EtOAC R$_f$=0.21 (trace R$_f$=0.5) UV+PMA. Product steaks to baseline.

Anal Calcd for $C_{14}H_{13}NO_2$: C, 73.99; H, 5.77; N, 6.16. Found: C, 73.94; H, 5.93; N, 5.94.

EXAMPLE 118

N-Hydroxy-N-benzyl-4-(4-phenylbutyl)benzamide

Following the procedure of Example 115 except substituting benzyl bromide for methyl iodide in Example 115 Part E, the title compound is obtained.

EXAMPLE 119

N-Hydroxy-N-allyl-4-(4-phenylbutyl)benzamide

Following the procedure of Example 115 except substituting allyl bromide for methyl iodide in Example 115 Part E, the title compound is obtained.

EXAMPLE 120

N-Hydroxy-N-phenyl[1,1'-biphenylyl]-4-carboxamide

Following the procedure of Example 117 except substituting N-phenylhydroxylamine hydrochloride for N-methylhydroxylamine hydrochloride in Example 117 Part B, the title compound is obtained.

EXAMPLE 121

N-Hydroxy-N-cyclohexyl[1,1-biphenylyl]-4-carboxamide

Following the procedure of Example 117 except substituting N-cyclohexylhydroxylamine hydrochloride for N-methylhydroxylamine hydrochloride in Example 117 Part B, the title compound is obtained.

EXAMPLE 122

N-Hydroxy-N-methyl-4-cyclohexylbenzamide

Following the procedure of Example 117 except substituting 4-cyclohexylbenzoic acid for 1,1'-biphenylcarboxylic acid in Part A, the title compound is obtained.

EXAMPLE 122a 3-(4-Phenylbutyl)-N-hydroxy-N-methylbenzamide

Following the procedure of Example 115 except substituting m-formylmethylbenzoate for p-formylmethylbenzoate in Part B, the title compound is obtained.

EXAMPLE 123

2-(4-Phenylbutyl)-N-hydroxy-N-methylbenzamide

Following the procedure of Example 115 except substituting o-formylmethylbenzoate for p-formylmethylbenzoate in Part B, the title compound is obtained.

EXAMPLE 124

4-(4-Phenylbutyl)-N-hydroxy-N-ethylbenzamide

Following the procedure of Example 115 except substituting ethyl iodide for methyl iodide, the title compound is obtained.

EXAMPLE 125

4-(4-Phenylbutyl)-N-hydroxy-N-benzylbenzamide

Following the procedure of Example 115 except substituting benzyl bromide for methyl iodide, the title compound is obtained.

EXAMPLE 126

4-(4-Phenylbutyl)-N-hydroxy-N-propylbenzamide

Following the procedure of Example 115 except substituting propyl iodide for methyl iodide, the title compound is obtained.

EXAMPLE 127

4-(4-Phenyl-1-butenyl)-N-hydroxy-N-butylbenzamide

Following the procedure of Examples 115 and 116 except substituting butyl iodide for methyl iodide in Example 115 Part E, the title compound is obtained.

EXAMPLE 128

N-Hydroxy-N-i-butyl[1,1'-biphenylyl]benzamide

Following the procedure of Example 117 except substituting i-butyl iodide for methyl iodide, the title compound is obtained.

EXAMPLE 129

N-Hydroxy-N-benzyl[1,1'-biphenylyl]benzamide

Following the procedure of Example 117 except substituting benzyl bromide for methyl iodide, the title compound is obtained.

EXAMPLE 130

N-Hydroxy-N-hexyl-4-cyclohexylbenzamide

Following the procedure of Example 122 except substituting hexyl iodide for methyl iodide, the title compound is obtained.

EXAMPLE 131

N-Hydroxy-N-phenethyl-4-cyclohexylbenzamide

Following the procedure of Example 122 except substituting phenethyl bromide for methyl iodide, the title compound is obtained.

EXAMPLES 132 to 140

Following the procedure of Example 115, exept substituting for the 1-bromo-3-phenylpropane the bromide shown in Table A, Column I, substituting for methyl iodide, the halide shown in Column II, the product dhown in Column III is obtained.

TABLE A

| Ex. No. | Column I R⁴Br R⁴ | Column II Hal R$^{1a}$ Hal R$^{1a}$ | Column III R⁴ | R$^{1a}$ |
|---|---|---|---|---|
| 132. | C₄H₉ | Br C₄H₉ | as in Col. I | as in Col. II |
| 133. | C₃H₇ | Br C₆H₅CH₂ | | |
| 134. | C₇H₁₅ | Br ⬡ | | |

Column III structure: phenyl–C(=O)–N(OH)–R$^{1a}$ with R⁴ substituent on phenyl.

TABLE A-continued

Column III $$R^4\text{-}C_6H_4\text{-}C(O)\text{-}N(R^{1a})\text{-}OH$$

| Ex. No. | Column I R⁴Br R⁴ | Column II Hal R¹ᵃ Hal | R¹ᵃ |
|---|---|---|---|
| 135. | C₆H₅(CH₂)₂ | Br | C₆H₅CH₂ |
| 136. | C₆H₅CH₂ | Br | C₂H₅ |
| 137. | C₉H₁₉ | I | C₆H₅CH₂ |
| 138. | C₆H₅—(CH₂)₅ | I | C₃H₇ |
| 139. | CH₃ | Br | CH₃ |
| 140. | C₂H₅ | I | C₅H₁₁ |

EXAMPLES 141 to 147

Following the procedure of Example 115 Part A to E and Example 116 except substituting the bromide shown in Column I of Table A for 1-bromo-3-phenyl-propane used in Example 115 Part A and substituting the halide shown in Column II of Table A for methyl iodide used in Example 115 Part E, the following compounds are obtained.

| Ex. No. | |
|---|---|
| 141. | C₃H₇—CH=CH—C₆H₄—C(O)—N(C₄H₉)—OH |
| 142. | CH₃CH₂—CH=CH—C₆H₄—C(O)—N(CH₂C₆H₅)—OH |
| 143. | CH₃—(CH₂)₅—CH=CH—C₆H₄—C(O)—N(cyclohexyl)—OH |
| 144. | C₆H₅—CH₂CH=CH—C₆H₄—C(O)—N(CH₂—C₆H₅)—OH |
| 145. | C₆H₅—CH=CH—C₆H₄—C(O)—N(C₂H₅)—OH |
| 146. | CH₃—(CH₂)₇—CH=CH—C₆H₄—C(O)—N(CH₂C₆H₅)—OH |
| 147. | C₆H₅(CH₂)₄—CH=CH—C₆H₄—C(O)—N(C₃H₇)—OH |

EXAMPLES 148 to 153

Following the procedure of Example 117 except substituting for N-methylhydroxylamine hydrochloride the hydroxylamine hydrochloride shown in column I of Table B set out below, the product of the invention shown in Column II is obtained.

TABLE B

| | Column I R¹—N(OH)(H) | Column II biphenyl-C(O)—N(R¹)—OH |
|---|---|---|
| Ex. No. | R¹ | R¹ |
| 148. | C₃H₇ | As per Column I |
| 149. | C₆H₅(CH₂)₃ | |
| 150. | CH₃CH=CH—CH₂— | |
| 151. | C₅H₁₁ | |
| 152. | C₆H₅—CH₂ | |
| 153. | cyclopentyl | |

EXAMPLES 154 to 159

Following the procedure of Example 122 except substituting for N-methylhydroxylamine hydrochloride the hydroxylamine hydrochloride shown in column I of Table C set out below, the product of the invention shown in Column II is obtained.

TABLE C

| | Column I R¹—N(OH)(H) | Column II cyclohexyl-C₆H₄-C(O)—N(R¹)—OH |
|---|---|---|
| Ex. No. | R¹ | R¹ |
| 154. | C₃H₇ | As per Column I |
| 155. | C₆H₅(CH₂)₃ | |
| 156. | CH₃CH=CH—CH₂— | |
| 157. | C₅H₁₁ | |
| 158. | C₆H₅—CH₂ | |
| 159. | cyclopentyl | |

EXAMPLE 160

N-Methoxy-N-methyl [1,1'-biphenylyl-]-4-carboxamide

To a stirring solution of N-hydroxy-N-methyl[1,1'-biphenylyl]-4-carboxamide (prepared as described in Example 117) (1.13 g, 5 mmol) under argon in 30 ml of dry toluene is added NaH (0.137 g, 5.5 mmol). The mixture is allowed to stir for 30 minutes, then CH₃I (2.13g, 15 mmol) is added. The mixture is heated to reflux and allowed to stir for 1 hour. The reaction is cooled and diluted with EtOAc and partitioned over 5% KHSO₄. The organic phase is washed with brine, dried over anhydrous Na₂SO₄ and evaporated to yield yellow oil which is chromatographed on LPS-1 silica gel eluting with (6:4) hexane:EtOAc. Product containing fractions are evaporated to give title product.

EXAMPLE 161 to 172

Following the procedure of Examples 1, 117 and 160 except substituting for the benzoic acid of Example 1, Part C, the acid shown in Column I of Table C set out below, substituting the hydroxylamine in Column II for N-methylhydroxyl amine, and substituting for methyl iodide, the alkyl halide set out in Column III, the product of the invention set out in Column IV is obtained.

combined to yield after concentration title compound, 1.5 g (93%) as a clear oil.

B. 4-(4-Phenylbutyl)benzoic acid, methyl ester

To a stirring solution of Part A ester (850 mg, 3.2 mmol) in 20 ml of $CH_3OH$ was added Pd/C (5%) 85 mg under argon. Hydrogen gas was added and the reaction was allowed to stir under $H_2$ (balloon) for 1 hour. The mixture was filtered (Millipore) and concentrated in vacuo to give title compound in the form of a clear oil, 850 mg (~100%).

TABLE C

| Ex. No. | Column I $R^3$ (position) | Column II $R^1$ | Column III $R^2$—Br $R^2$ | Column IV $R^3$ | $R^1$ | $R^2$ |
|---|---|---|---|---|---|---|
| 161. | $C_6H_5$ (2) | $C_3H_7$ | $C_2H_5$ | as in Col. I | as in Col. II | as in Col. III |
| 162. | $C_6H_5$ (3) | $C_6H_5(CH_2)_3$ | $C_3H_7$ | | | |
| 163. | $C_6H_5$ (4) | $CH_3CH=CH-CH_2$ | $C_4H_9$ | | | |
| 164. | $C_6H_5$ (2) | $C_5H_{11}$ | $C_5H_{11}$ | | | |
| 165. | $C_6H_5$ (3) | $C_6H_5-CH_2$ | $CH_3$ | | | |
| 166. | $C_6H_5$ (4) | cyclopentyl | $CH_3$ | | | |
| 167. | cyclohexyl (4) | $C_3H_7$ | $C_2H_5$ | | | |
| 168. | cyclopentyl (3) | $C_6H_5(CH_2)_3$ | $C_3H_7$ | | | |
| 169. | cyclohexyl (3) | $CH_3CH=CH-CH_2$ | $C_4H_9$ | | | |
| 170. | cycloheptyl (2) | $C_5H_{11}$ | $C_5H_{11}$ | | | |
| 171. | cyclohexyl (2) | $C_6H_5CH_2$ | $CH_3$ | | | |
| 172. | cyclohexyl (4) | $C_6H_5CH_2$ | $CH_3$ | | | |

EXAMPLE 73

N-(1,1-Dimethylethyl)-N-hydroxy-(4-phenylbutyl)-benzamide

A. 4-(4-Phenyl-1-butenyl)benzoic acid, methyl ester

To a 0° solution of phenylpropyl triphenylphosphonium bromide (3.55 g, 1.25 eq) in 30 ml of dry THF under argon was added K-t-amylate (3.9 ml, 1.1 eq). After stirring for 30 minutes at 0° C. then allowing to warm to room temperature, a solution of 4-formylbenzoic acid methyl ester (1.0 g, 6.1 mmol) in ~8 ml of dry THF was added dropwise. This solution was stirred for 3 hours at room temperature, then diluted with ~1 ml of $H_2O$, and concentrated to remove most of the THF. EtOAc (~200 ml) was added and the mixture was washed with $H_2O$, 1N HCl (2×) and brine. After drying over anhydrous $MgSO_4$, the solvent was removed in vacuo to yield a yellow oil which solidified soon after. Column purification of this crude product was done on a 50 mm column on silica gel eluted with 95:5 hexane/EtOAc. Product containing fractions were C. 4-(4-Phenylbutyl)-benzoic acid A solution of Part B (850 mg; 3.2 mmol), 2N NaOH (4.8 ml, 3.0 eq) in 35 ml of $CH_3OH/THF$ (5:1) was heated to reflux for 2½ hours. The solution was acidified with 1N HCl (15 ml). THF was removed in vacuo and a white solid was collected by filtration. This solid was dissolved in EtOAc and washed with ½ saturated brine, then brine. After drying over anhydrous $MgSO_4$, concentration gave title acid 680 mg as a white solid. The filtrate, from the original filtration, was extracted with EtOAc 2×(75 ml portions), washed with ½ saturated brine, then brine. Concentration after drying over anhydrous $MgSO_4$ gave title acid 800 mg, a total yield of 91%.

D.
N-(1,1-Dimethylethyl)-N-hydroxy-4-(4-phenylbutyl)-benzamide

To a stirring solution of Part C acid (350 mg, 1.4 mmol) in 10 ml of dry benzene under argon, was added oxalyl chloride (0.13 ml, 2.0 eq). To this solution was added DMF dropwise in 10 minute intervals, until no gas evol ed and the solution turned slightly cloudy (two drops). The mixture was stirred for 1 hour, then reduced on the rotovap without heating. The crude product was dissolved in 5 ml of THF and added dropwise to a 0° C. solution of N-t-butylhydroxylamine hydrochloride (325 mg, 2.0 ec) in 20 ml of THF:H$_2$O (1:1) with triethylamine (0.59 ml, 3.0 eq). The solution was stirred for ½ hour at 0° C., then allowed to warm to room temperature and stir for 4 hours. The reaction mixture was diluted with EtOAc and the organic layer was washed with H$_2$O, 1N HCl (2×), and brine, then dried over anhydrous MgSO$_4$. Concentration in vacuo gave a yellow oil which gave a white solid (187 mg) with the addition of hexane. Recrystallization of this solid from hexane/EtOAc gave title product, 153 mg (35%).

TLC (1:1) Hexane:EtOAc R$_f$=0.41 UV+CeMo. Product streaks to baseline.

Anal Calcd for C$_{21}$H$_{27}$NO$_2$: C, 77.50; H, 8.36; N, 4.30. Found: C, 77.28; H, 8.43; N, 4.37.

EXAMPLE 174
N-Hydroxy-N-phenyl-4-(4-phenylbutyl)benzamide

To a stirring solution of 4-(4-phenylbutyl)benzoic acid (prepared as described in Example 173) (370 mg, 1.45 mmol) in 10 ml of dry benzene under argon, was added oxalyl chloride (0.14 ml, 2.0 eq.). To this solution was added DMF dropwise in 10 minute intervals, until no gas was evolved and the solution turned slightly cloudy (2 drops). The mixture was stirred for 1 hour, then reduced on the rotovap without heating. The crude product was dissolved in 5 ml of THF and added dropwise to a 0° C. solution of N-phenyl hydroxylamine (317 mg, 2.0 eq.) in 20 ml of THF:H$_2$O (1:1) with triethylamine (0.41 ml, 2.0 eq.). The solution was stirred for 1 hour at 0° C., then allowed to warm to room temperature and stir overnight. The reaction mixture was diluted with EtOAc and the organic layer was washed with H$_2$O, 1N HCl (2×), and brine, then dried over anhydrous MgSO$_4$. Concentration in vacuo gave a white solid which was triturated with hexane to remove a yellow impurity and recrystallized from hot hexane/EtOAc, to give title product, 256 mg (51%).

TLC (1:1) Hexane:EtOAc R$_f$=0.46. Trace R$_f$=0.62. UV+CeMO.

Product streaks to baseline. Anal Calcd for C$_{23}$H$_{23}$NO$_2$: C, 79.97; H, 6.71; N, 4.05. Found: C, 79.62; H, 6.56; N, 3.92.

EXAMPLE 175
N-(1,1-Dimethylethyl)-N-hydroxy[1,1'-biphenylyl]-4-carboxamide To a stirring solution of 1,1'-biphenylcarboxylic acid (1.0 g, 5.1 mmol) in 10 ml of dry benzene under argon, was added oxalyl chloride (0.48 ml, 2.0 eq.). To this solution was added DMF dropwise in 10 minute intervals, until no gas was evolved and the solution turned slightly cloudy (2 drops). The mixture was stirred for 1 hour and then reduced on the rotovap without heating. The crude product, a white solid, was dissolved in 5 ml of THF and added dropwise to a 0° C. solution of N-t-butylhydroxylamine hydrochloride (1.0 g, 1.6 eq.) in 20 ml of THF:H$_2$O (1:1) with triethylamine (2.0 ml, 3.0 eq.). The solution was stirred for 1 hour at 0° C., then allowed to warm to room temperature and stirred overnight. The reaction mixture was diluted with EtOAc and the organic layer was washed with H$_2$O, 1N HCl (2×), and brine, then dried over anhydrous MgSO$_4$. Concentration in vacuo gave a white solid which was recrystallized from hot hexane/EtOAc, to give title product, 540 mg (40%), as long white needles.

TLC (1:1) Hexane:EtOAc R$_f$=0.42. Trace R$_f$=0.68. UV+CeMO. Product streaks to baseline.

Anal Calcd for C$_{17}$H$_{19}$NO$_2$: C, 75.81; H,, 7.11; N, 5.20. Found: C, 75.74; H, 7.21; N, 5.21.

EXAMPLE 176
N-Cyclohexyl-N-hydroxy[1,1'-biphenylyl]-4-carboxamide

To a stirring solution of 1,1'-biphenyl carboxylic acid (500 mg, 2.5 mmol) in 10 ml of dry benzene under argon was added oxalyl chloride (0.24 ml, 1.1 eq.). To this solution was added DMF dropwise in 10 minute intervals until no gas was evolved and the solution turned slightly cloudy (two drops). The mixture was stirred for 1 hour then reduced on the rotovap without heating. The crude product, a white solid, was dissolved in THF (5 ml) and added dropwise to a 0° C. solution of N-cyclohexylhydroxylamine hydrochloride (766 mg, 2 eq.) in 20 ml of THF:H$_2$O (1:1) with triethylamine (1.1 ml, 3.0 eq.) added sequentially. The solution was stirred for 0.5 hour at 0° C. then allowed to warm to room temperature and stir for an additional 6 hours. The reaction mixture was diluted with EtOAc and the organic layer was washed with H$_2$O, 1N HCl (2×). and brine, then dried over anhydrous MgSO$_4$. Concentration in vacuo gave a white solid which was recrystallized from hot hexane/EtOAc to give title product, 615 mg (82%) as long white needles.

TLC (1:1) Hexane:EtOAc R$_f$=0.46, trace R$_f$=0.54 UV+PMA. Product streaks to baseline.

Anal calcd for C$_{19}$H$_{21}$NO$_2$: C, 77.26; H, 7.17; N, 4.74. Found: C, 77.24; H, 7.13; N, 4.65.

EXAMPLE 177
N-Hydroxy-N-methyl-4-pentylbenzamide

To a 0° C. solution of N-methylhydroxylamine hydrochloride (793 mg, 2 eq.) in 20 ml of THF:H$_2$O (1:1) with triethylamine (198 ml, 3.0 eq.) was added 4-(n-pentyl) benzoic acid chloride (1.0 ml, 4.75 mmol). The solution was stirred for 0.5 hour at 0° C. then allowed to warm to room temperature and stir overnight. The reaction mixture was diluted with EtOAc and the organic layer was washed with H$_2$O, 1N HCl (2×), and brine, then dried over anhydrous MgSO$_4$. Concentration in vacuo gave a yellow oil which was flash chromatographed in LPS-1 silica gel eluting with (1:1) hexane/EtOAc. Product containing fractions were concentrated in vacuo to yield title product, 380 mg (37%) as a light yellow oil.

TLC (1:1) Hexane:EtOAc, R$_f$=0.29, UV+PMA. Product streaks to baseline.

Anal Calcd for C$_{13}$H$_{19}$NO$_2$: C, 70.56; H, 8.65; N, 6.33. Found: C, 70.73; H, 8.58; N, 6.08.

EXAMPLE 78

4-Heptyl-N-hydroxy-N-methylbenzamide

To a 0° C. solution of N-methylhydroxylamine hydrochloride (701 mg, 2 eq.) in 20 ml of THF:H$_2$O (1:1) with triethylamine (1.75 ml, 3.0 eq.) was added 4-n-heptyl benzoic acid chloride (1.0 g, 4.2 mmol). The solution was stirred for ½ hour at 0° C. then allowed to warm to room temperature and stir overnight. The reaction mixture was diluted with EtOAc and the organic layer washed with H$_2$O, 1N HCl (2×), and brine, then dried over anhydrous MgSO$_4$. Concentration in vacuo gave an oil which was flash chromatographed on LPS-1 silica gel eluting with (1:1) hexane:EtOAc. Product containing fractions were concentrated in vacuo to yield title product, 448 mg (43%) as a light yellow oil which solidified upon standing. TLC (1:1) Hexane:EtOAc R$_f$=0.18, UV+PMA. Product streaks to baseline.

Anal Calcd for C$_{15}$H$_{23}$NO$_2$: C, 72.25; H, 9.30; N, 5.62. Found: C, 72.30; H, 9.36; N, 5.43.

EXAMPLE 179

4-(Cyclohexyloxy)-N-hydroxy-N-methylbenzamide

A. 4-(1-Cyclohexenyloxy)benzoic acid

To a stirred solution of p-hydroxybenzoic acid (1.38 gm, 10 mmol) in THF (30 ml) is added sodium hydride (0.48 g, 20 mmol), followed by cyclohexenyl bromide (1.63 gm 10 mM). The mixture is heated to reflux for 12 hours. After cooling the reaction mixture is poured into ethyl acetate and extracted with 1N NaOH (3×). The combined aqueous extracts are combined, acidified to pH 2 with concentrated HCl, and extracted 3× with ethyl acetate. The combined organic extracts are dried over Na$_2$SO$_4$ and evaporated under reduced pressure to afford the product.

B. 4-(Cyclohexyloxy)benzoic acid

To a stirring solution of Part A acid (500 mg, 2.3 mmol) in 20 ml of CH$_3$OH/EtOAc (1:1) was added rhodium/alumina (5%) 50 mg under argon. Hydrogen gas was added and the reaction was allowed to stir under H$_2$ (balloon) for ½ hour. The mixture was filtered (Millipore) and concentrated in vacuo to yield a white solid which was carried directly on to the next step.

C. 4-(Cyclohexyloxy)-N-hydroxy-N-methylbenzamide

To a stirring solution of Part B acid (375 mg, 1.7 mmol) in 10 ml of dry benzene under argon, was added oxalyl chloride (0.16 ml, 1.1 eq.). To this solution was added DMF dropwise in 10 minute intervals, until no gas was evolved and the solution turned slightly cloudy (2 drops). The mixture was stirred for 1 hour and then reduced on the rotovap without heating. The crude product, mixed with 5 ml of THF, was added dropwise to a 0° C. solution of N-methylhydroxylamine hydrochloride (284 mg, 2 eq.) in 20 ml of THF:H$_2$O (1:1) with triethylamine (0.71 ml, 3.0 eq.). The solution was stirred for ½ hour at 0° C., then allowed to warm to room temperature and stir overnight. The reaction mixture was diluted with EtOAc and the organic layer washed with H$_2$O, 1N HCl in vacuo gave a white solid which was recrystallized from hexane/EtOAc to give title product, 277 mg (88%).

TLC (1:1) Hexane:EtOAc R$_f$=0.19, UV+CeMO. Product streaks to baseline.

Anal Calcd for C$_{14}$H$_{19}$NO$_3$: C, 67.45; H, 7.68; N, 5.62. Found: C, 67.44; H, 7.71; N, 5.40.

EXAMPLE 180

N-Hydroxy-N-methyl-4-(3-phenylpropoxy)benzamide

A. 4-(3-Phenylpropoxy)benzoic acid, methyl ester

To a solution of p-hydroxybenzoic acid, methyl ester (2.0 g, 13.2 mmol) in toluene/DMF (2:1) under argon was added NaH (630 mg, 2.0 eq.). After stirring for 15 minutes 3-phenylpropyl bromide (3.0 ml, 1.5 eq.) was added and the mixture refluxed for 4 hours. The solution was diluted with EtOAc and water. The organic layer was washed with H$_2$O, 5% KHSO$_4$ and brine, then dried over anhydrous MgSO$_4$. Concentration in vacuo gave a yellow oil which solidified upon standing. Recrystallization from hexane/EtOAc gave title compound, a cream colored solid, 1.35 g (38%).

B. 4-(3-Phenylpropoxy)benzoic acid

To a stirred solution of the Part A methyl ester (1.35 g, 5.0 mmol) in CH$_3$OH (60 ml) and THF (10 ml) was added a 2.0N NaOH solution (7.5 ml, 3.0 eq.) and the mixture was refluxed under argon overnight, then quenched with 0.25M citric acid. Concentration in vacuo, followed by dilution with EtOAc and washes of H$_2$O, 1N HCl, and brine, gave a white solid after concentration and drying over anhydrous MgSO$_4$. Recrystallization from hexane/EtOAc gave title acid, 1.04 g (81%).

C. N-Hydroxy-N-methyl-4-(3-phenylpropoxy)benzamide

To a stirring solution of Part B acid (300 mg, 1.17 mmol) in 10 ml of dry benzene under argon was added oxalyl chloride (0.57 ml, 3.8 eq.). To this solution was added DMF dropwise in 10 minute intervals, until no gas was evolved and the solution turned slightly cloudy (2 drops). The mixture was stirred for 24 hours, then reduced on the rotovap without heating. The crude product, a white solid, was diluted with 5 ml of THF and added dropwise to a 0° C. solution of N-methylhydroxylamine hydrochloride (195 mg, 2 eq.) in 20 ml of THF:H$_2$O (1:1) with triethylamine (0.5 ml, 3.0 eq.). The solution was stirred for ½ hour at 0° C. then allowed to warm to room temperature and stir, overnight. The reaction mixture was diluted with EtOAc and the organic layer was washed with H$_2$O, 1N HCl (2×), and brine, then dried over anhydrous MgSO$_4$. Concentration in vacuo gave a white solid which was recrystallized from hot hexane/EtOAc, to give title product, 286 mg (91%).

TLC (1:1) Hexane:EtOAc R$_f$=0.17, UV+CeMO. Product streaks to baseline.

Anal Calcd for C$_{17}$H$_{17}$NO$_3$: C, 71.56; H, 6.71; N, 4.91. Found: C, 71.84; H, 6.84; N, 4.82.

EXAMPLE 181

N-Hydroxy-4-(4-phenylbutyl)-N-(phenylmethyl)benzamide

A. 4-(4-Phenylbutyl)-N-(tetrahydropyran-2-yloxy)benzamide

To a 0° C. solution of 4-(4-phenylbutyl)benzoic acid (700 mg, 2.8 mmol) in 40 ml of CH$_2$Cl$_2$ under argon was added tetrahydropyranyl hydroxylamine (H$_2$N-OTHP) (654 mg, 2.0 eq.), 1-hydroxybenzotriazole (HOBt) (460 mg, 1.2 eq.), N,N'-dicyclohexylcarbodiimide (700 mg, 1.2 eq.) sequentially. After 0.5 hour at 0° the solution was allowed to warm to room temperature and stir under argon for 4 hours. The solution was filtered, concentrated in vacuo to yield a white solid which was chromatographed on LPS-1 silica gel eluting with 6:4 hexane/EtOAc. Product containing fractions were evaporated to give title compound, an oil 1.0 g (~100%).

B.
4-(4-Phenylbutyl)-N-(phenylmethyl)-N-(tetrahydropyran-2-yloxy)benzamide

To a stirring solution of Part A compound (350 mg, 1.0 mmol) under argon in 10 ml of dry toluene was added NaH (1.1 eq., 27 mg). The mixture was allowed to stir for 30 minutes and then benzyl bromide (0.37 ml, 3.0 eq.) was added. The mixture was heated to reflux and allowed to stir for 1.5 hours. The reaction was cooled and diluted with EtOAc and partitioned over 5% $KHSO_4$. The organic phase was washed with brine, dried over anhydrous $MgSO_4$ and evaporated to yield yellow oil which was chromatographed on LPS-1 silica gel eluting with hexane:EtOAc. Product containing fractions were evaporated to give title compound (240 mg, 59%) as a pale yellow oil.

C.
N-Hydroxy-4-(4-phenylbutyl)-N-(phenylmethyl)benzamide

To a stirring solution of Part B compound (240 mg, 0.6 mmol) in 10 ml of $CH_3OH$ under argon was added pyridinium-p-toluenesulfonate (178 mg; 1.2 eq.). The solution was heated to 60° C. in an oil bath for 24 hours. The solution was diluted with EtOAc and washed with 10 ml of brine, diluted with 10 ml of water. The organic layer was washed with brine (10 ml) and dried over $MgSO_4$ (anhydrous) and reduced in vacuo to yield an off-white solid which was recrystallized from hexane/EtOAc to give title product (130 mg, 62%) as a white solid with m.p. 83.5°–85.0° C.

TLC (2:1) hexane-EtOAc; $R_f$=0.29, UV+CeMO. Product streaks to baseline.

Anal Calcd for $C_{24}H_{25}NO_2$: C, 80.19; H, 7.01; N, 3.90. Found: C, 79.94; H, 7.08; N, 3.77.

What is claimed is:

1. A compound having the structure

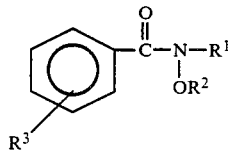

wherein
$R^1$ is lower alkyl, aryl, lower alkenyl aralkyl, or

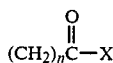

wherein n is 2 to 4 and X is hydroxy, alkoxy, amino, $C_1$–$C_4$-alkylamino or $C_1$–$C_4$-dialkylamino;
$R^2$ is hydrogen or lower alkyl; and
$R^3$ is $C_1$–$C_{20}$ alkyl, $C_3$–$C_{20}$ alkenyl, aryl, aryl-alkyl, cycloalkyl, aryl-alkenyl, lower alkoxy, lower alkenyloxy, aryl-alkoxy, aryloxy or cycloalkyloxy, including pharmaceutically acceptable monobasic and dibasic salts whereof, and wherein the term alkyl by itself or as part of another group is unsubstituted or substituted with a substituent which is a halo, trifluoromethyl, alkoxy, aryl, alkyl-aryl, haloaryl, cycloalkyl, alkylcycloalkyl, hydroxy, alkylamino, alkanoylamino, arylcarbonylamino, nitro, cyano, thiol or an alkylthio substituent, the term aryl by itself or as part of another group is unsubstituted or substituted with 1 or 2 halogens, 1 or 2 lower alkyl groups, 1 or 2 lower alkoxy groups, an aryl group, 1 or 2 hydroxyls, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkythio groups; and the term cycloalkyl by itself or as Part of another group is unsubstituted or substituted with 1 or 2 halogens 1 or 2 lower alkyl groups, 1 or 2 alkoxy groups, an aryl group, 1 or 2 hydroxyls, 1 or 2 alkylamino groups, 1 or 2 alkanoylamino, 1 or 2 arylcarbonylamino groups, 1 or 2 amino groups, 1 or 2 nitro groups, 1 or 2 cyano groups, 1 or 2 thiol groups and/or 1 or 2 alkylthio groups.

2. The compound as defined in claim 1 wherein $R^1$ is alkyl or

3. The compound as defined in claim 1 wherein $R^1$ is alkyl, $R^2$ is H and $R^3$ is alkyl.

4. The compound as defined in claim 1 wherein $R^1$ is phenyl, phenylalkyl, phenylalkenyl, C to $C_{20}$ alkyl or $C_3$ to $C_{20}$ alkenyl.

5. The compound as defined in claim 1 having the name 4-decyl-N-hydroxy-N-methylbenzamide.

6. The compound as defined in claim 1 having the name (Z)-4-[[4-(1-decenyl)benzoyl]hydroxyamino]butanoic acid.

7. The compound as defined in claim 1 having the name (Z)-4-[[4-(1-decenyl)benzoyl]hydroxyamino]butanoic acid including all stereoisomers thereof.

8. The compound as defined in claim 1 having the name 4-[(3-decylbenzoyl)hydroxyamino]butanoic acid.

9. The compound as defined in claim 1 having the name 4-[(2-decylbenzoyl)hydroxyamino]butanoic acid or its dilithium salt.

10. The compound as defined in claim 1 having the name 4-[(4-decylbenzoyl)hydroxyamino]butanoic acid, ethyl ester.

11. The compound as defined in claim I having the name, (Z)-4-[[4-(1-decenyl)benzoyl]methoxyamino]butanoic acid or its dicyclohexylamine salt(1:1) including all stereoisomers thereof.

12. The compound as defined in claim 1 having the name N-(4-amino-4-oxobutyl)-4-decyl-N-hydroxybenzamide.

13. The compound as defined in claim 1 having the name 4-[(4-decylbenzoyl)hydroxyamino]butanoic acid.

14. The compound as defined in claim 1 having the name 5-[(4-decylbenzoyl)hydroxyamino]pentanoic acid.

15. The compound as defined in claim 1 having the name (4-decyl-N-hydroxybenzamido)acetic acid.

16. The compound as defined in claim 1 having the name 4-[[3-(1-decenyl)benzoyl]hydroxyamino]butanoic acid.

17. The compound as defined in claim 1 having the name (Z)-4-(1-decenyl)-N-hydroxybenzamide, including all stereoisomers thereof.

18. The compound as defined in claim 1 having the name N-hydroxy-N-methyl-4-(4-phenylbutyl)benzamide.

19. The compound as defined in claim 1 having the name N-hydroxy-N-methyl[1,1'-biphenylyl]-4-carboxamide.

20. The compound as defined in claim 1 having the name N-hydroxy-N-methyl-4-(4-phenylbuten-1-yl)benzamide.

21. The compound as defined in claim 1 having the name N-hydroxy-4-(4-phenylbutyl)-N-(phenylmethyl)-benzamide.

22. The compound as defined in claim 1 having the name N-hydroxy-N-phenyl-4-(4-phenylbutyl)benzamide.

23. The compound as defined in claim 1 having the name N-(1,1-dimethylethyl)-N-hydroxy[1,1'-biphenylyl]-4-carboxamide.

24. The compound as defined in claim 1 having the name N-cyclohexyl-N-hydroxy[1,1'-biphenylyl]-4-carboxamide.

25. The compound as defined in claim 1 having the name N-hydroxy-N-methyl-4-pentylbenzamide.

26. The compound as defined in claim 1 having the name 4-heptyl-N-hydroxy-N-methylbenzamide.

27. The compound as defined in claim 1 having the name 4-(cyclohexyloxy)-N-hydroxy-N-methylbenzamide.

28. The compound as defined in claim 1 having the name N-hydroxy-N-methyl-4-(3-phenylpropoxy)benzamide.

29. The compound as defined in claim 1 having the name N-(1,1-dimethylethyl)-N-hydroxy-4-(4-phenylbutyl)benzamide.

30. A composition for inhibiting allergic conditions in a mammalian species, comprising an effective amount of a compound as defined in claim 1 or a pharmaceutically acceptable salt thereof, and a pharmaceutically acceptable carrier thereof.

31. A method of inhibiting $\Delta^5$-lipoxygenase which comprises administering to the circulatory system of a mammalian host an effective amount of a compound as defined in claim 1 or a pharmaceutically acceptable salt thereof.

32. The method as defined in claim 30 wherein said compound is administered in an amount within the range of from about 1 to about 100 mg/kg.

33. A method for treating asthma in a mammalian species in need of such treatment, which comprises administering to a mammalian host an effective amount of a compound as defined in claim 1 or a pharmaceutically acceptable salt thereof.

* * * * *